(12) United States Patent
Parham et al.

(10) Patent No.: US 12,241,012 B2
(45) Date of Patent: Mar. 4, 2025

(54) HETEROCYCLIC COMPOUNDS FOR LIQUID CRYSTALS

(71) Applicant: MERCK PATENT GMBH, Darmstadt (DE)

(72) Inventors: Amir Hossain Parham, Darmstadt (DE); Constanze Brocke, Darmstadt (DE); Carsten Fritzsch, Darmstadt (DE); Dagmar Klass, Darmstadt (DE); Matthias Jost, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 18/238,331

(22) Filed: Aug. 25, 2023

(65) Prior Publication Data

US 2024/0101903 A1    Mar. 28, 2024

(51) Int. Cl.
| | |
|---|---|
| G02F 1/1333 | (2006.01) |
| C07D 285/14 | (2006.01) |
| C09K 19/34 | (2006.01) |
| H01Q 1/36 | (2006.01) |

(52) U.S. Cl.
CPC ........ C09K 19/3497 (2013.01); C07D 285/14 (2013.01); H01Q 1/36 (2013.01)

(58) Field of Classification Search
CPC .............. C09K 19/34; C09K 19/3491; C09K 19/3497; C09K 2019/181; C09K 2019/183; C09K 2019/3009; C09K 2019/301; C09K 2019/3016; C09K 2019/3021; C07D 285/14; G02F 1/1333
See application file for complete search history.

(56) References Cited

U.S. PATENT DOCUMENTS

| | | | |
|---|---|---|---|
| 7,361,288 B2 | 4/2008 | Lüssem et al. | |
| 10,711,138 B2 | 7/2020 | Kirsch et al. | |
| 11,180,698 B2 | 11/2021 | Wittek et al. | |
| 2007/0073055 A1 | 3/2007 | Organ et al. | |
| 2016/0200697 A1 | 7/2016 | Rebbaa et al. | |
| 2022/0025264 A1 | 1/2022 | Ikeuchi et al. | |
| 2024/0101903 A1* | 3/2024 | Parham ................ C07D 285/14 |

FOREIGN PATENT DOCUMENTS

| | | |
|---|---|---|
| CN | 110128231 A | 8/2019 |
| DE | 102004029429 A1 | 2/2005 |
| DE | 102012004393 A1 | 9/2012 |
| WO | 2017137145 A1 | 8/2017 |
| WO | 2017174619 A1 | 10/2017 |
| WO | 2022129018 A1 | 6/2022 |

OTHER PUBLICATIONS

X. Qin et al., "Palladium-Catalyzed Desulfitative Cross-Coupling of Arylsulfonyl Hydrazides with Terminal Alkynes: A General Approach toward Functionalized Internal Alkynes" Anal. Chem. 2020, 92, 924-931.

L.-W. Qian et al., "Alkyne/Ruthenium(II) Complex-Based Ratiometric Surface-Enhanced Raman Scattering Nanoprobe for In Vitro and Ex Vivo Tracking of Carbon Monoxide" J. Org. Chem. 2017, 82, 6764-6769.

Office Action in corresponding EP application 23193111.4 dated Jan. 15, 2024 (pp. 1-9).

* cited by examiner

*Primary Examiner* — Geraldina Visconti

(74) *Attorney, Agent, or Firm* — Millen, White, Zelano, & Branigan Scaba Henter

(57) ABSTRACT

Compounds of formula I

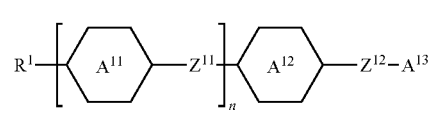

liquid crystal media containing these compounds, and high-frequency components containing these media, especially microwave components for high-frequency devices, such as devices for shifting the phase of microwaves, tunable filters, tunable metamaterial structures, and electronic beam steering antennas, phased array antennas, and devices containing these components, and furthermore optical components containing these liquid-crystalline media, operable in the infrared region of the electromagnetic spectrum.

17 Claims, No Drawings

HETEROCYCLIC COMPOUNDS FOR LIQUID CRYSTALS

The present invention relates to benzothiadiazol compounds and related structures as liquid crystals, to liquid crystal media comprising said compounds, and to high-frequency components comprising these media, especially microwave components for high-frequency devices, such as devices for shifting the phase of microwaves, tunable filters, tunable metamaterial structures, and electronic beam steering antennas (e.g. phased array antennas), and to devices comprising said components. The invention further relates to an optical component comprising said liquid-crystalline media operable in the infrared region of the electromagnetic spectrum. The invention further relates to the use of said LC medium in the infrared (IR) region and to devices comprising said optical component.

Liquid-crystalline media have been used for many years in electro-optical displays (liquid crystal displays: LCDs) in order to display information. More recently, however, liquid-crystalline media have also been proposed for use in components for microwave technology, such as, for example, in DE 10 2004 029 429 A and in JP 2005-120208 (A).

A. Gaebler, F. Goelden, S. Müller, A. Penirschke and R. Jakoby "Direct Simulation of Material Permittivites using an Eigen-Susceptibility Formulation of the Vector Variational Approach", 12MTC 2009—International Instrumentation and Measurement Technology Conference, Singapore, 2009 (IEEE), pp. 463-467, describe the corresponding properties of the known liquid-crystal mixture E7 (Merck KGaA, Germany).

DE 10 2004 029 429 A describes the use of liquid-crystal media in microwave technology, inter alia in phase shifters. Therein, liquid-crystalline media and their properties in the micro-wave frequency range have been discussed. The liquid-crystalline media therein are mainly based on mixtures of aromatic nitriles and isothiocyanates. In the publication WO 2017/137145 A1 compounds and mixtures for high frequency applications are described that comprise benzothiadiazole compounds like the structure depicted below.

Similar structures are provided in WO 2017/174619 A1. The benzothiadiazole compounds used therein are substituted in 4,7-position. In contrast to these citations, the current invention is centered on compounds having the heterocycle as an end group, not as an intermediate ring group. The benzo ring therein is substituted at the 5-position.

Development in the area of liquid-crystalline materials for the use in microwave applications is far from complete. In order to improve the properties of microwave devices, attempts are constantly being made to develop novel compounds which enable such devices to be optimised. For use in high-frequency technology, liquid-crystalline media having particular, hitherto rather unusual, uncommon properties, or combinations of properties, are required.

Novel compounds with improved properties for use in liquid-crystalline media are thus necessary. In particular, the loss in the microwave range must be reduced or the tunability ($\tau$) enhanced to improve the material quality ($\eta$, aka figure of merit).

In addition, there is a demand for an improvement in the low-temperature behaviour of the components. An improvement in both the operating properties and also in the shelf life is desirable.

An object of the present invention is thus to provide compounds having advantageous properties for use in liquid-crystalline media for the use in components for microwave applications. Another object of the present invention is to provide a liquid crystalline medium with improved properties relevant for the application in the microwave range of the electromagnetic spectrum.

The object of the invention is achieved by the compound of the formula I

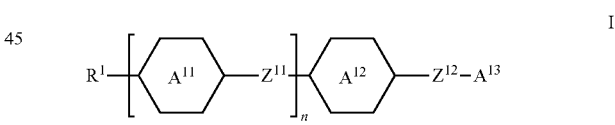

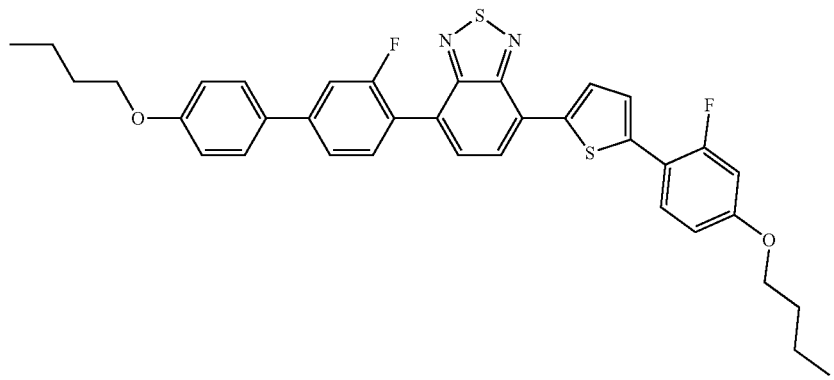 [SMILES: CCCCOc1ccc(-c2ccc(-c3ccc(-c4ccc(-c5ccc(OCCCC)cc5F)s4)c4nsnc34)c(F)c2)cc1]

in which
A[13] denotes

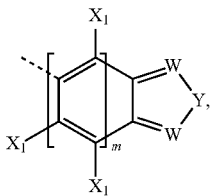

wherein m is 0 or 1,
where explicitly above formula for A[13] denotes

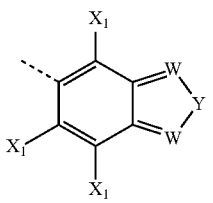

for m=1, which is preferred, or

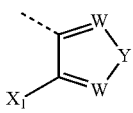

for m=0,
more preferably A[13] denotes any of the partial structures

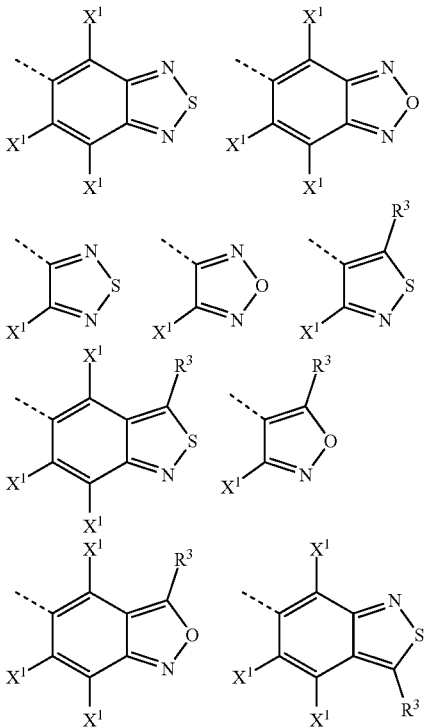

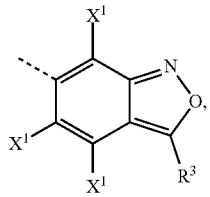

W is independently N or CR[3], preferably at least one of the groups W is N, most preferably both groups W are N, Y is S or O, preferably S, X[1] independently on each occurrence denotes H, F, —CH$_3$, —C$_2$H$_5$ or Cl, preferably H or F, most preferably H, R[3] denotes H, F, Cl, CH$_3$, C$_2$H$_5$, preferably H, R[1] denotes H, straight chain or branched alkyl having 1 to 12 C atoms or alkenyl having 2 to 12 C atoms, in which one or more CH$_2$-groups may be replaced by

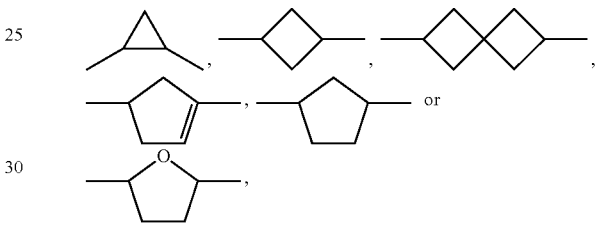

where one or more non-adjacent CH$_2$-groups may be replaced by O and/or S, and where one or more H atoms may be replaced by F;

Z[11], Z[12] identically or differently, denote a single bond, —C≡C—, —CH═CH—, —CF═CF—, —CH═CF—, —CF═CH— or —C≡C—C≡C—,

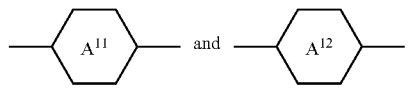

independently denote a radical selected from the following groups:

a) the group consisting of 1,4-phenylene, 1,4-naphthylene, 2,6-naphthylene, tetralin-5,8-diyl, and tetralin-2,6-diyl, in which one or two CH groups may be replaced by N and in which one or more H atoms may be replaced by a group L, b) the group consisting of trans-1,4-cyclohexylene, 1,4-cyclohexenylene, bicyclo[1.1.1]pentane-1,3-diyl, 4,4'-bicyclohexylene, bicyclo[2.2.2]octane-1,4-diyl, and spiro[3.3]heptane-2,6-diyl, in which one or more non-adjacent CH$_2$ groups may be replaced by —O— and/or —S— and in which one or more H atoms may be replaced by F or alkyl having 1 to 6 C atoms, c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms, and n is 0, 1 or 2.

The invention further relates to liquid crystalline media comprising one or more of the compounds of formula I.

Preferred embodiments of the present invention are subject-matter of the dependent claims or can also be taken from the description.

Surprisingly, the compounds of formula I are distinguished by a favourably high tunability and low loss in the microwave range of the electromagnetic spectrum. They enable liquid-crystalline media having excellent stability and at the same time a high dielectric anisotropy, suitably fast switching times and a suitable, nematic phase range.

In particular, media comprising a compound according to the invention are distinguished by an improved figure-of-merit $\eta$ due to lower loss and a higher tunability $\tau$.

The media according to the present invention are distinguished by a high clearing temperature, a broad nematic phase range and excellent low-temperature stability (LTS). As a result, devices containing the media are operable under extreme temperature conditions.

The media are further distinguished by high values of the dielectric anisotropy and low rotational viscosities. As a result, the threshold voltage, i.e. the minimum voltage at which a device is switchable, is very low. A low operating voltage and low threshold voltage is desired in order to enable a device having improved switching characteristics and high energy efficiency. Low rotational viscosities enable fast switching of the devices according to the invention.

These properties as a whole make the media comprising the compound of formula I particularly suitable for use in components and devices for high-frequency technology and applications in the microwave range, in particular devices for shifting the phase of microwaves, tunable filters, tunable metamaterial structures, and electronic beam steering antennas (e.g. phased array antennas).

According to another aspect of the present invention there is thus provided a component and a device comprising said component, both operable in the microwave region of the electromagnetic spectrum. Preferred components are phase shifters, varactors, wireless and radio wave antenna arrays, matching circuits and adaptive filters.

The medium according to the invention is likewise suitable for use in the visible or infrared region of the electromagnetic spectrum.

The invention thus further relates to the use of the compound of formula I and the medium comprising one or more compounds of formula I in the visible or infrared region of the electromagnetic spectrum, preferably in the VIS, A-band, and/or B-band and/or C-band, for phase modulation of said visible light or infrared light.

According to another aspect of the present invention there is provided an optical component comprising the liquid crystal medium according to the invention sandwiched between a pair of substrates.

The invention further relates to a device comprising the optical component according to the invention. Preferred devices are infrared imagers, wavelength selective switches, LCoS-SLM, LIDAR systems, wavelength-division multiplexing (WDM) systems, reconfigurable optical add-drop multiplexer (ROADM), and nonmechanical beam steering, e.g. steerable Electro Evanescent Optical Refraction (SEEOR) prism as published in the article P. McManamon, 2006, "Agile Nonmechanical Beam Steering," Opt. Photon. News 17(3): 24-29.

According to another aspect of the present invention there is provided a method of spatially modulating visible or infrared light, the method comprising, i) providing an optical component comprising first and second substrates facing each other and each having a surface, the first substrate comprising at least one first electrode, the second substrate comprising at least one second electrode, the component further comprising a liquid crystal layer sandwiched between the first and second substrates wherein the liquid crystal comprises one or more compounds of the formula I above;

ii) receiving incident infrared light at a surface of said optical component;

iii) applying a predetermined voltage to each of the individual electrodes formed on the first substrate in order to modulate a refractive index of the liquid crystal layer.

According to another aspect of the present invention there is provided a method of manufacturing an optical phase modulator, comprising at least the steps of a) providing a first substrate with a first electrode, optionally having a two dimensional array of individually electrically drivable cells;

b) depositing a liquid crystal medium as set forth herein, said medium containing a compound of formula I, over the first substrate; and c) mounting a second substrate with a second electrode onto the liquid crystal material.

The optical component according to the invention is distinguished by excellent operational stability when exposed to the environment because of high clearing temperature, broad nematic phase range and excellent low-temperature stability (LTS) of the liquid crystal medium used therein. As a result, the component and devices containing the component are operable under extreme temperature conditions.

Herein, "high-frequency technology" means applications of electromagnetic radiation having frequencies in the range of from 1 MHz to 1 THz, preferably from 1 GHz to 500 GHz, more preferably 2 GHz to 300 GHz, particularly preferably from about 5 GHz to 150 GHz.

As used herein, infrared region of the electromagnetic spectrum is taken to mean the spectral region of electromagnetic radiation having a wavelength in the range of from 0.75 μm to 1000 μm.

As used herein, visible light (VIS) is taken to mean the spectral region of electromagnetic radiation having a wavelength in the range of from 380 nm to 750 nm.

As used herein, infrared A (IR-A) is taken to mean the spectral region of electromagnetic radiation having a wavelength in the range of from 0.75 μm to 1.4 μm.

As used herein, infrared B (IR-B) is taken to mean the spectral region of electromagnetic radiation having a wavelength in the range of from 1.4 μm to 3 μm.

As used herein, infrared C (IR-C) is taken to mean the spectral region of electromagnetic radiation having a wavelength in the range of from 3 μm to 1000 μm.

Preferably, the optical component according to the invention operates at a wavelength in the range of from 750 nm to 2500 nm, in particular from 1530 nm to 1565 nm.

A very preferred light source for applications according to the invention is an IR laser emitting light with a wavelength of 1,55 μm or an IR laser emitting light with a wavelength of 905 nm.

As used herein, halogen is F, Cl, Br or I, preferably F or Cl, particularly preferably F.

Herein, alkyl is straight-chain or branched or cyclic and has 1 to 15 C atoms, is preferably straight-chain and has, unless indicated otherwise, 1, 2, 3, 4, 5, 6 or 7 C atoms and is accordingly preferably methyl, ethyl, n-propyl, n-butyl, n-pentyl, n-hexyl or n-heptyl.

Herein, branched alkyl is preferably isopropyl, s-butyl, isobutyl, isopentyl, 2-methylbutyl, 2-methylhexyl or 2-ethylhexyl.

As used herein, cyclic alkyl is taken to mean straight-chain or branched alkyl or alkenyl having up to 12 C atoms, preferably alkyl having 1 to 7 C atoms, in which a group $CH_2$ is replaced with a carbocyclic ring having 3 to 5 C atoms, very preferably selected from the group consisting of cyclopropylalkyl, cyclobutylalkyl, cyclopentylalkyl and cyclopentenylalkyl.

Herein, an alkoxy radical is straight-chain or branched and contains 1 to 15 C atoms. It is preferably straight-chain and has, unless indicated otherwise, 1, 2, 3, 4, 5, 6 or 7 C atoms and is accordingly preferably methoxy, ethoxy, n-propoxy, n-butoxy, n-pentoxy, n-hexoxy or n-heptoxy.

Herein, an alkenyl radical is preferably an alkenyl radical having 2 to 15 C atoms, which is straight-chain or branched and contains at least one C—C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4-or -5-enyl, hept-1-, -2-, -3-, -4-, -5- or -6-enyl. If the two C atoms of the C—C double bond are substituted, the alkenyl radical can be in the form of E and/or Z isomer (trans/cis). In general, the respective E isomers are preferred. Of the alkenyl radicals, prop-2-enyl, but-2- and -3-enyl, and pent-3- and -4-enyl are particularly preferred.

Herein, alkynyl is taken to mean an alkynyl radical having 2 to 15 C atoms, which is straight-chain or branched and contains at least one C-C triple bond. 1- and 2-propynyl and 1-, 2- and 3-butynyl are preferred.

In case $R^F$ denotes a halogenated alkyl-, alkoxy-, alkenyl or alkenyloxy it can be branched or unbranched. Preferably it is unbranched, mono-poly or perfluorinated, preferably perfluorinated and has 1, 2, 3, 4, 5, 6 or 7 C atoms, in case of alkenyl 2, 3, 4, 5, 6 or 7 C atoms.

The compounds of the general formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for said reactions. Use can be made here of variants which are known per se, but are not mentioned here in greater detail.

If desired, the starting materials can also be formed in situ by not isolating them from the reaction mixture, but instead by immediately reacting them further into the compounds of the general formula I.

A preferred synthetic pathway towards compounds of formula I having an alkyne bridging group is shown in scheme 1. The terminal arylalkynes (1) are obtained by standard processes as described for example in the article: Marta Pytlarczyk & Przemyslaw Kula (2019) Synthesis and mesomorphic properties of 4,4"-dialkynyl-2',3'-difluoro-p-terphenyls—the influence of C≡C acetylene linking bridge, Liquid Crystals, 46:4, 618-628, DOI: 10.1080/02678292.2018.1515376. The alkynes can be coupled catalytically with aromatic bromides (Sonogashira) of the heterocycles like 5-bromobenzothidiazole or analogous compounds to afford the substituted alkyne (2). Alternatively a trimethylsilyl acetylene is introduced as a building block, which can be likewise coupled with aromatic bromides.

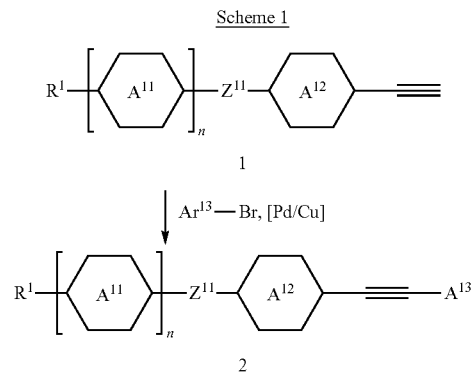

Scheme 1

The following definitions are independently preferred for the compounds of the formula I and its sub-formulae:

$R^1$ denotes H, non-fluorinated alkyl having 1 to 12 C atoms, or non-fluorinated alkenyl having 2 to 12 C atoms, in which one or more $CH_2$-groups may be replaced by

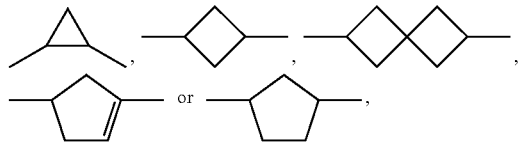

where one or more non-adjacent $CH_2$-groups may be replaced by O, very preferably alkyl having 1 to 7 C atoms,

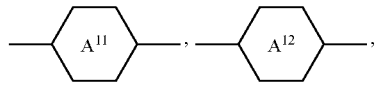

on each occurrence, independently of one another, denote

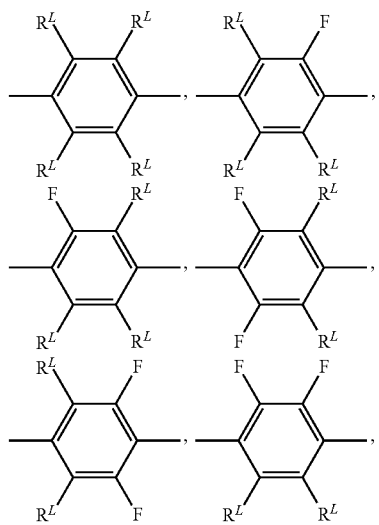

-continued

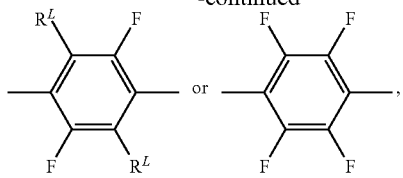

in which $R^L$, on each occurrence, identically or differently, denotes H, Cl or alkyl having 1 to 6 C atoms, preferably H, Cl, methyl or ethyl, very preferably H, Cl or methyl, and in particular H,
or denote

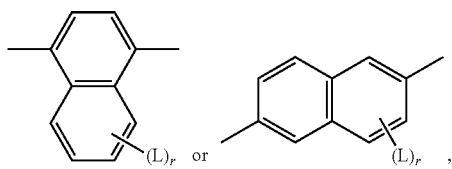

very preferably

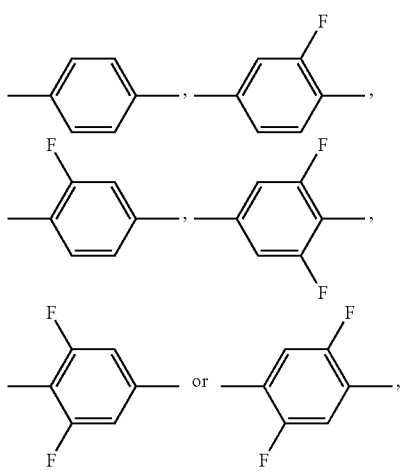

L denotes F or alkyl having 1 to 6 C atoms, and
r is 0, 1, 2, 3, 4, 5 or 6, preferably 0 or 1, and wherein

alternatively denotes

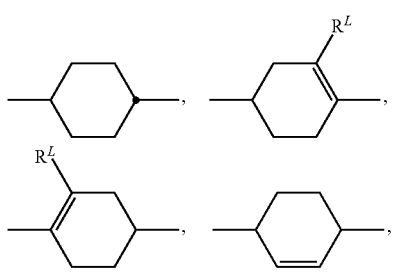

-continued

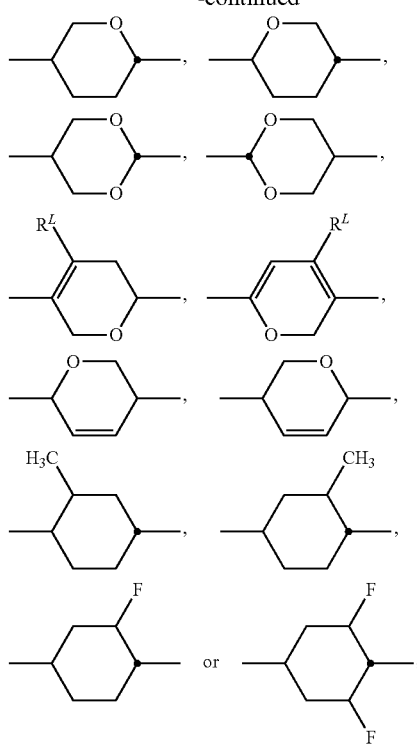

in which $R^L$ denotes H or methyl, preferably H;
preferably

and
n is 0, 1 or 2, preferably 0 or 1,
$A^{13}$ is a group selected from the formulae

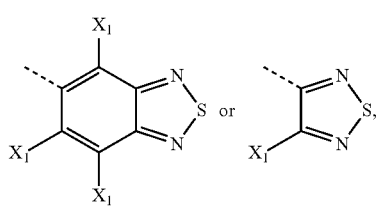

more preferably of formula

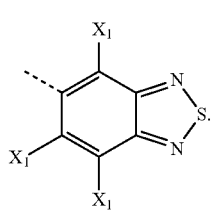

The partial group

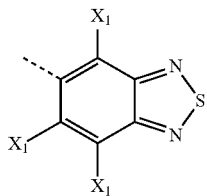

preferably is a group of formulae

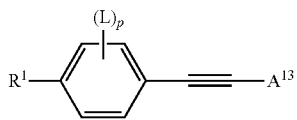

Preferably, the compounds of the formula I are selected from the compounds of the formulae Ia, Ib:

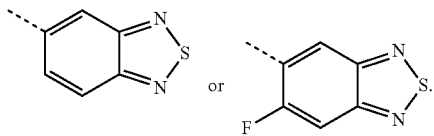
Ia

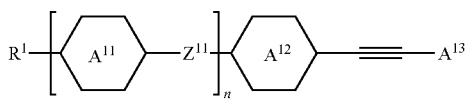
Ib in which the occurring groups and parameters have the meanings defined above.

The compounds of the formula Ia are preferably selected from the compounds of the following sub-formulae:

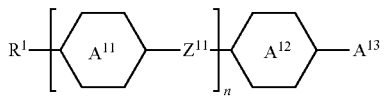
Ia-1

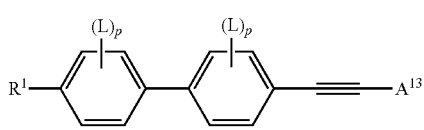
Ia-2

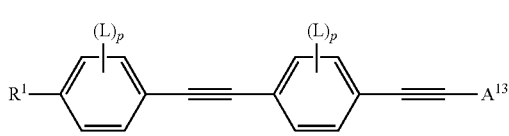
Ia-3 in which the occurring groups have the meanings given above for formula I.

The compounds of the formula Ib are preferably selected from the compounds of the following sub-formulae:

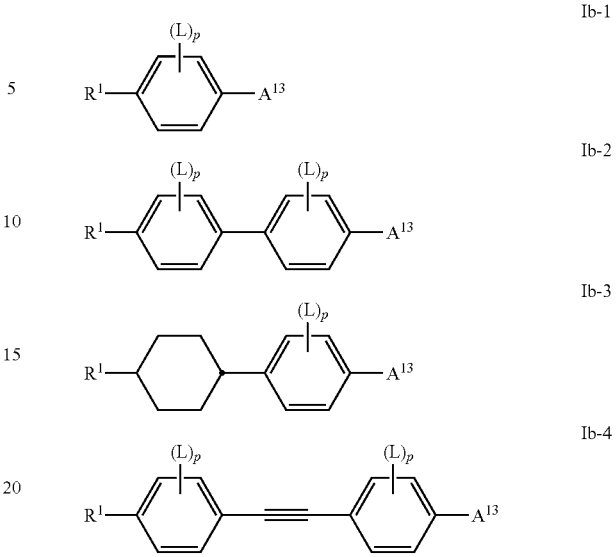
Ib-1
Ib-2
Ib-3
Ib-4 in which the occurring groups have the meanings given above for formula I, and p is 0, 1, 2, 3 or 4, preferably 0, 1 or 2.

In a preferred embodiment, the compounds of formula I are selected from the compounds of formula Ic

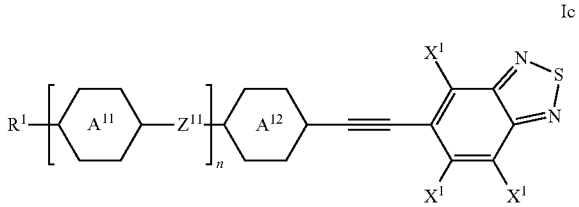
Ic in which
R$^1$,

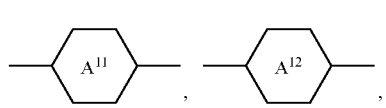

Z$^{11}$, X$^1$ and n have the meanings given above for formula I, and n is preferably 0 or 1.

The compound of formula Ic is preferably selected from the group consisting of the formulae Ic-1, Ic-2 and Ic-3:

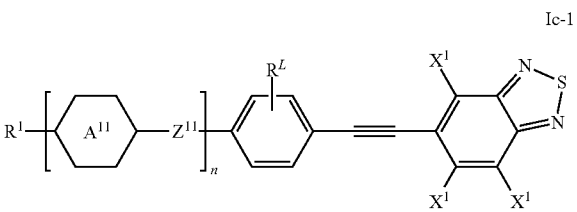
Ic-1

-continued

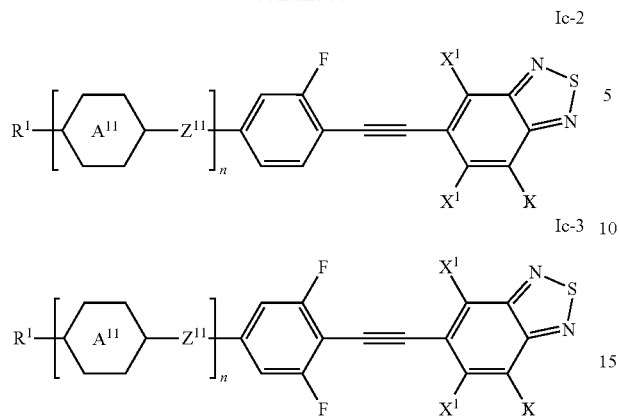

in which R¹,

$R^L$, $Z^{11}$, $X^1$ and n have the respective meanings given above for formula I and its sub-formulae.

The present invention therefore also relates to a liquid-crystalline medium comprising two or more liquid-crystalline compounds, comprising one or more compounds of the general formula I.

The liquid-crystalline media in accordance with the present invention comprise one or more compounds of the formula I and optionally at least one further, preferably mesogenic compound. The liquid-crystal medium therefore preferably comprises two or more compounds which are preferably liquid-crystalline. Preferred media comprise the preferred compounds of the formula I.

Further components of the liquid-crystalline media are preferably selected from the compounds of the formula II:

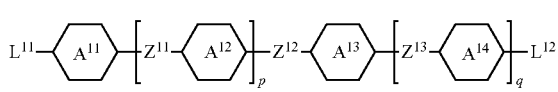
II in which
$L^{11}$ denotes $R^{11}$ or $X^{11}$,
$L^{12}$ denotes $R^{12}$ or $X^{12}$,
$R^{11}$ and $R^{12}$, independently of one another, denote non-fluorinated alkyl or non-fluorinated alkoxy having 1 to 17, preferably having 3 to 10, C atoms or non-fluorinated alkenyl, non-fluorinated alkynyl, non-fluorinated alkenyloxy or non-fluorinated alkoxy-alkyl having 2 to 15, preferably 3 to 10, C atoms, preferably alkyl or non-fluorinated alkenyl,
$X^{11}$ and $X^{12}$, independently of one another, denote F, Cl, Br, —CN, —NCS, —SCN, $SF_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably $CF_3$, $OCF_3$, Cl, F or NCS,
p and q, independently of one another, denote 0 or 1,
$Z^{11}$ to $Z^{13}$, independently of one another, denote trans-CH=CH—, trans-CF=CF—, —C≡C— or a single bond,

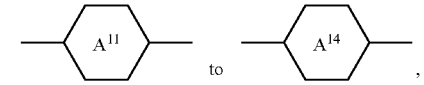

independently of one another, denote

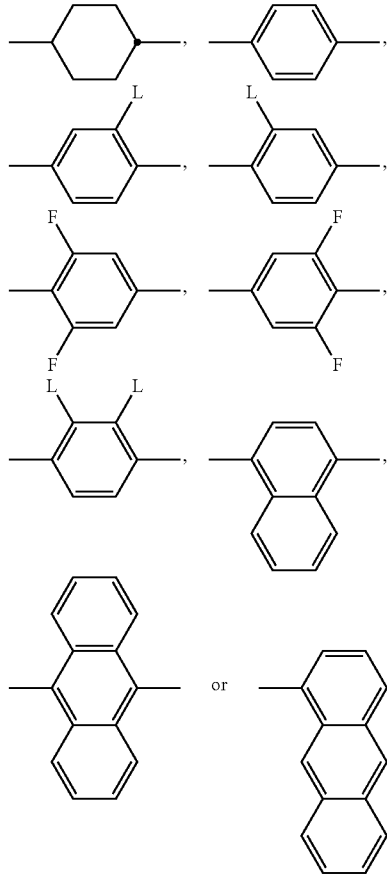

and
L on each occurrence, independently of one another, denotes branched or unbranched alkyl, alkenyl or alkynyl having 1 or 2 to 12 C atoms, resp., in which, independently of one another, one or more $CH_2$ groups may also be replaced by O, or denotes $C_3$-$C_6$ cycloalkyl, $C_3$-$C_6$ cycloalkenyl, fluorinated alkyl or alkenyl, fluorinated alkoxy or alkenyloxy, F, Cl, Br, CN, NCS, SCN or $SF_5$.

In a preferred embodiment of the present invention, the liquid-crystalline media comprise one or more compounds of the formula I and one or more compounds of the formula II.

The liquid-crystalline media in accordance with the present application preferably comprise in total 1 to 50%, preferably 2 to 40% and particularly preferably 3 to 30%, of compounds of the formula I.

The liquid-crystalline media in accordance with the present application preferably comprise in total 10 to 100%, preferably 20 to 95% and particularly preferably 25 to 90%, of compounds of the formulae I and II.

In accordance with the present invention, the compounds of the formula II are preferably used in a total concentration of 10% to 90%, more preferably 15% to 85%, even more preferably 25% to 80% and very preferably 30% to 75%, of the mixture as a whole.

In addition, the liquid-crystalline media may comprise further additives, such as stabilisers, chiral dopants, dichroic dyes and nanoparticles. The individual, added compounds are employed in concentrations of 0.005 to 6%, preferably 0.1 to 3%. The total concentration of these further constituents is in the range from 0% to 10%, preferably 0.1% to 6%, based on the mixture as a whole. However, the concentration data for the remaining constituents of the liquid-crystal mixtures, i.e. the liquid-crystalline or mesogenic compounds, are indicated without taking into account the concentration of these additives.

The liquid-crystalline media preferably comprise 0 to 10% by weight, in particular 0.01 to 5% by weight and particularly preferably 0.1 to 3% by weight, of stabilisers. The media preferably comprise one or more stabilisers selected from 2,6-di-tert-butylphenols, 2,2,6,6-tetramethylpiperidines or 2-benzotriazol-2-ylphenols. These assistants are known to the person skilled in the art and are commercially available, for example as light stabilisers.

In the present application, the expression dielectrically positive describes compounds or components where $\Delta\varepsilon > 3.0$, dielectrically neutral describes those where $-1.5 \leq \Delta\varepsilon \leq 3.0$ and dielectrically negative describes those where $\Delta\varepsilon < -1.5$. $\Delta\varepsilon$ is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 µm. The voltage applied is a rectangular wave having a frequency of 1 kHz and an effective value of typically 0.5 V to 1.0 V, but it is always selected to be below the capacitive threshold of the respective test mixture.

$\Delta\varepsilon$ is defined as $(\varepsilon_\| - \varepsilon_\perp)$, while $\varepsilon_{ave.}$ is $(\varepsilon_\| + 2\varepsilon_\perp)/3$.

The host mixture used for the determination of physical constants of pure compounds by extrapolation is ZLI-4792 or Base mixture H1 from Merck KGaA, Germany. The absolute values of the dielectric constants, the birefringence ($\Delta n$) and the rotational viscosity ($\gamma_1$) of the compounds are determined from the change in the respective values of the host mixture on addition of the compounds. The concentration in the host is 10% or in case of insufficient solubility 5%. The values are extrapolated to a concentration of 100% of the added compounds.

In the examples, the phase sequences of pure compounds are given using the following abbreviations:

K: crystalline, N: nematic, SmA: smectic A, SmB: smectic B, I: isotropic.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees (Kelvin). All physical properties are determined in accordance with "Merck Liquid Crystals, Physical Properties of Liquid Crystals", Status November 1997, Merck KGaA, Germany, and are quoted for a temperature of 20° C., unless expressly stated otherwise. The optical aniso-tropy ($\Delta n$) is determined at a wavelength of 589.3 nm. The dielectric anisotropy ($\Delta\varepsilon$) is determined at a frequency of 1 kHz. The threshold voltages, as well as all other electro-optical properties, are determined using test cells produced at Merck KGaA, Germany. The test cells for the determination of $\Delta\varepsilon$ have a cell thickness of approximately 20 µm. The electrode is a circular ITO electrode having an area of 1.13 cm$^2$ and a guard ring. The orientation layers are SE-1211 from Nissan Chemicals, Japan, for homeotropic orientation ($\varepsilon_\|$) and polyimide AL-1054 from Japan Synthetic Rubber, Japan, for homogeneous orientation ($\varepsilon_\perp$). The capacitances are determined using a Solatron 1260 frequency response analyser using a sine wave with a voltage of 0.3 V$_{rms}$. The light used in the electro-optical measurements is white light. A set-up using a commercially available DMS instrument from Autronic-Melchers, Germany, is used here. The charac-teristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency range as described in A. Penirschke et al. "Cavity Perturbation Method for Characterization of Liquid Crystals up to 35 GHz", 34$^{th}$ European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) or quartz capillary. The capillary has an inner diameter of 0.5 mm and an outer diameter of 0.78 mm. The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the frequency depending response of the cavity is recorded using a commercial vector network analyser (N5227A PNA Microwave Network Analyzer, Keysight Technologies Inc. USA). For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in the above-mentioned publication A. Penirschke et al., 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla.

Preferred components are phase shifters, varactors, wireless and radio wave antenna arrays, matching circuit adaptive filters and others.

In the present application, the term compounds is taken to mean both one compound and a plurality of compounds, unless expressly stated otherwise.

All mixtures according to the invention are nematic. The liquid-crystal media according to the invention preferably have nematic phases in preferred ranges given above. The expression have a nematic phase here means on the one hand that no smectic phase and no crystallisation are observed at low temperatures at the corresponding temperature and on the other hand that no clearing occurs on heating from the nematic phase. At high temperatures, the clearing point is measured in capillaries by conventional methods. The investigation at low temperatures is carried out in a flow viscometer at the corresponding temperature and checked by storage of bulk samples: The storage stability in the bulk (LTS) of the media according to the invention at a given temperature T is determined by visual inspection. 2 g of the media of interest are filled into a closed glass vessel (bottle) of appropriate size placed in a refrigerator at a predetermined temperature. The bottles are checked at defined time intervals for the occurrence of smectic phases or crystallisation. For every material and at each temperature two bottles are stored. If crystallisation or the appearance of a smectic phase is observed in at least one of the two correspondent bottles the test is terminated and the time of the last inspection before the one at which the occurrence of a higher ordered phase is observed is recorded as the respective storage stability. The test is finally terminated after 1000 h, i.e an LTS value of 1000 h means that the mixture is stable at the given temperature for at least 1000 h.

The liquid crystals employed preferably have a positive dielectric anisotropy. This is preferably 2 or more, preferably 4 or more, particularly preferably 6 or more and very particularly preferably 10 or more.

Furthermore, the liquid-crystal media according to the invention are characterised by high anisotropy values in the microwave range. The birefringence at about 19 GHz is, for example, preferably 0.14 or more, particularly preferably 0.15 or more, particularly preferably 0.20 or more, particularly preferably 0.25 or more and very particularly preferably 0.30 or more. In addition, the birefringence is preferably 0.80 or less.

The dielectric anisotropy in the microwave range is defined as $$\Delta\varepsilon \equiv (\varepsilon_{r,\parallel} - \varepsilon_{r,\perp}).$$

The tunability ($\tau$) is defined as $$\tau \equiv (\Delta\varepsilon_r / \varepsilon_{r,\parallel}).$$

The material quality ($\eta$) is defined as $$\eta \equiv (\tau / \tan \delta_{\varepsilon_r, max}), \text{ where}$$

the maximum dielectric loss is $$\tan \delta_{\varepsilon_r, max} \equiv \max. \{\tan \delta_{\varepsilon r, \perp}; \tan \delta_{\varepsilon_r, \parallel}\}.$$

The tunability $\tau$ of the medium according to the invention, measured at 20° C. and 19 GHz is 0.250 or more, preferably 0.300 or more, 0.310 or more, 0.320 or more, 0.330 or more, or 0.340 or more, very preferably 0.345 or more and in particular 0.350 or more.

The material quality ($\eta$) of the preferred liquid-crystal materials is 6 or more, preferably 8 or more, preferably 10 or more, preferably 15 or more, preferably 17 or more, preferably 20 or more, particularly preferably 25 or more and very particularly preferably 30 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In some embodiments, however, liquid crystals having a negative value of the dielectric anisotropy can also advantageously be used.

The liquid crystals employed are either individual substances or mixtures. They preferably have a nematic phase.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.02% to 3%. The concentration of these and similar additives is not taken into consideration when quoting the values and concentration ranges of the liquid-crystal components and liquid-crystal compounds of the liquid-crystal media in this application.

Preferably the media according to the present invention comprise one or more chiral compounds as chiral dopants in order to adjust their cholesteric pitch. Their total concentration in the media according to the instant invention is preferably in the range 0.05% to 15%, more preferably from 1% to 10% and most preferably from 2% to 6%.

Optionally the media according to the present invention may comprise further liquid crystal compounds in order to adjust the physical properties. Such compounds are known to the skilled person. Their concentration in the media according to the instant invention is preferably 0% to 30%, more preferably 0.1% to 20% and most preferably 1% to 15%.

The response times are given as rise time ($\tau_{on}$) for the time for the change of the relative tuning, respectively of the relative contrast for the electro-optical response, from 0% to 90% ($t_{90}-t_0$), i.e. including the delay time ($t_{10}-t_0$), as decay time ($\tau_{off}$) for the time for the change of the relative tuning, respectively of the relative contrast for the electro-optical response, from 100% back to 10% ($t_{100}-t_{10}$) and as the total response time ($\tau_{total}=\tau_{on}-\tau_{off}$) respectively.

The liquid-crystal media according to the invention consist of a plurality of compounds, preferably 3 to 30, more preferably 4 to 20 and very preferably 4 to 16 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called pre-mixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present invention and especially in the following examples, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_lH_{2l-1}$, and $C_nH_{2n-1}$, $C_mH_{2m-1}$ and $C_lH_{2l-1}$ denote straight-chain alkyl or alkylene, respectively, in each case having n, m or l C atoms, wherein n and m, independently are 1, 2, 3, 4, 5, 6 or 7 and l is 1, 2 or 3. Table A lists the codes used for the ring elements of the core structures of the compounds, while Table B shows the linking groups and end groups. Table C shows illustrative structures of compounds with their respective abbreviations.

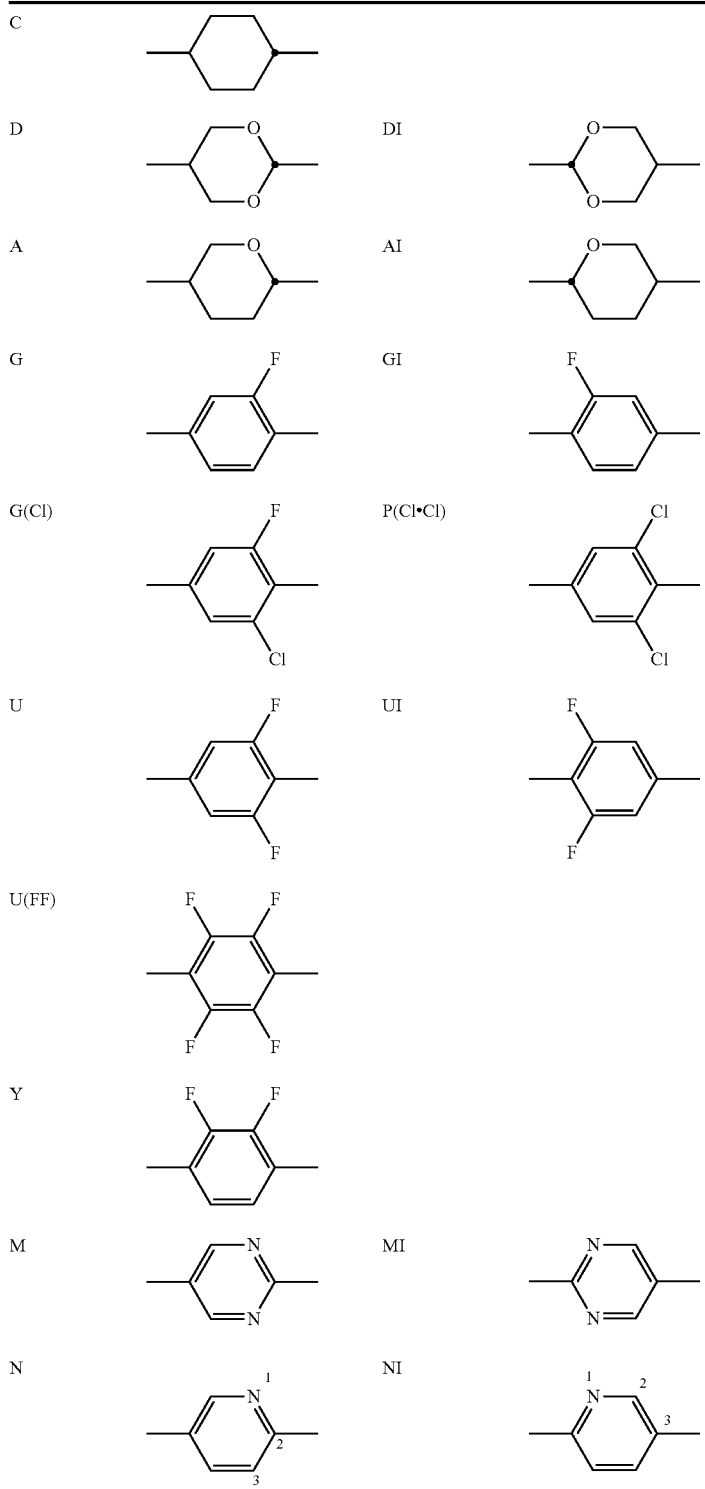

-continued
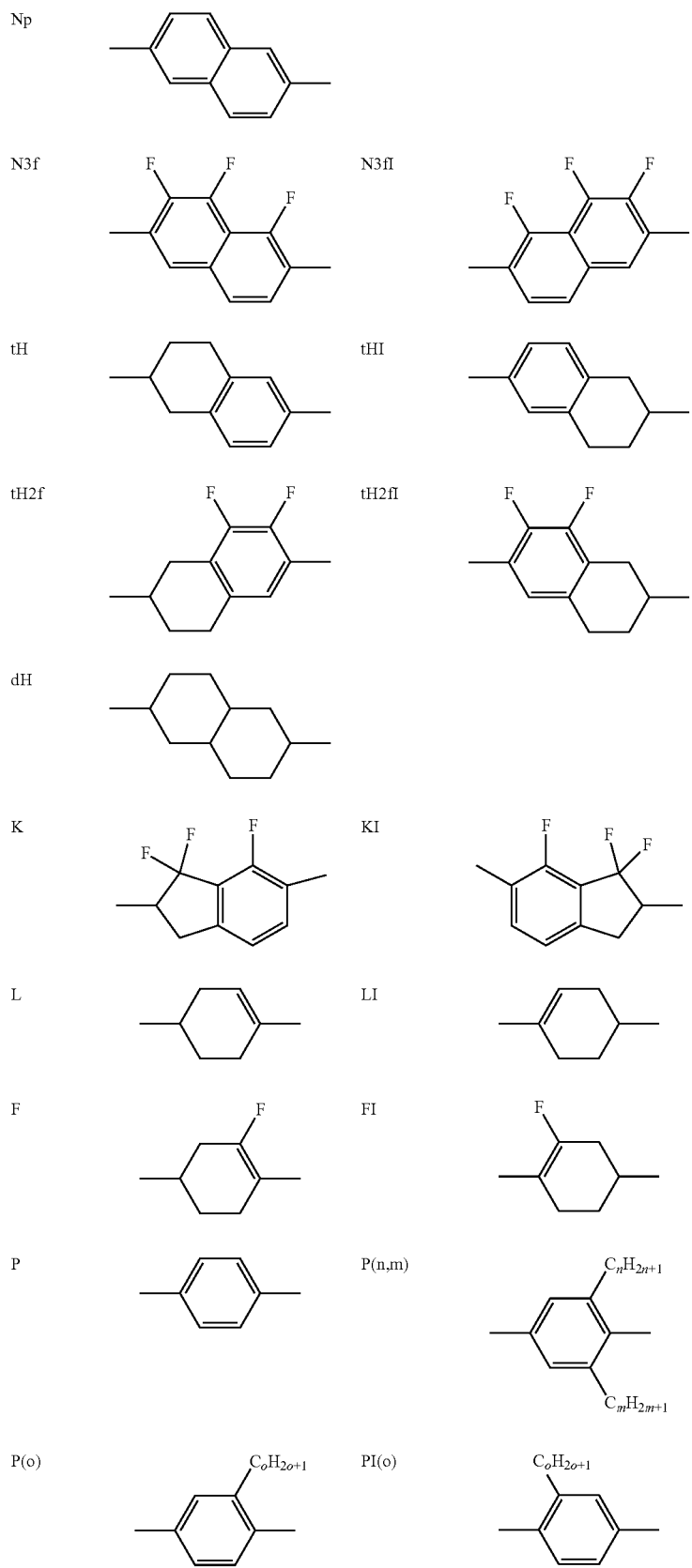

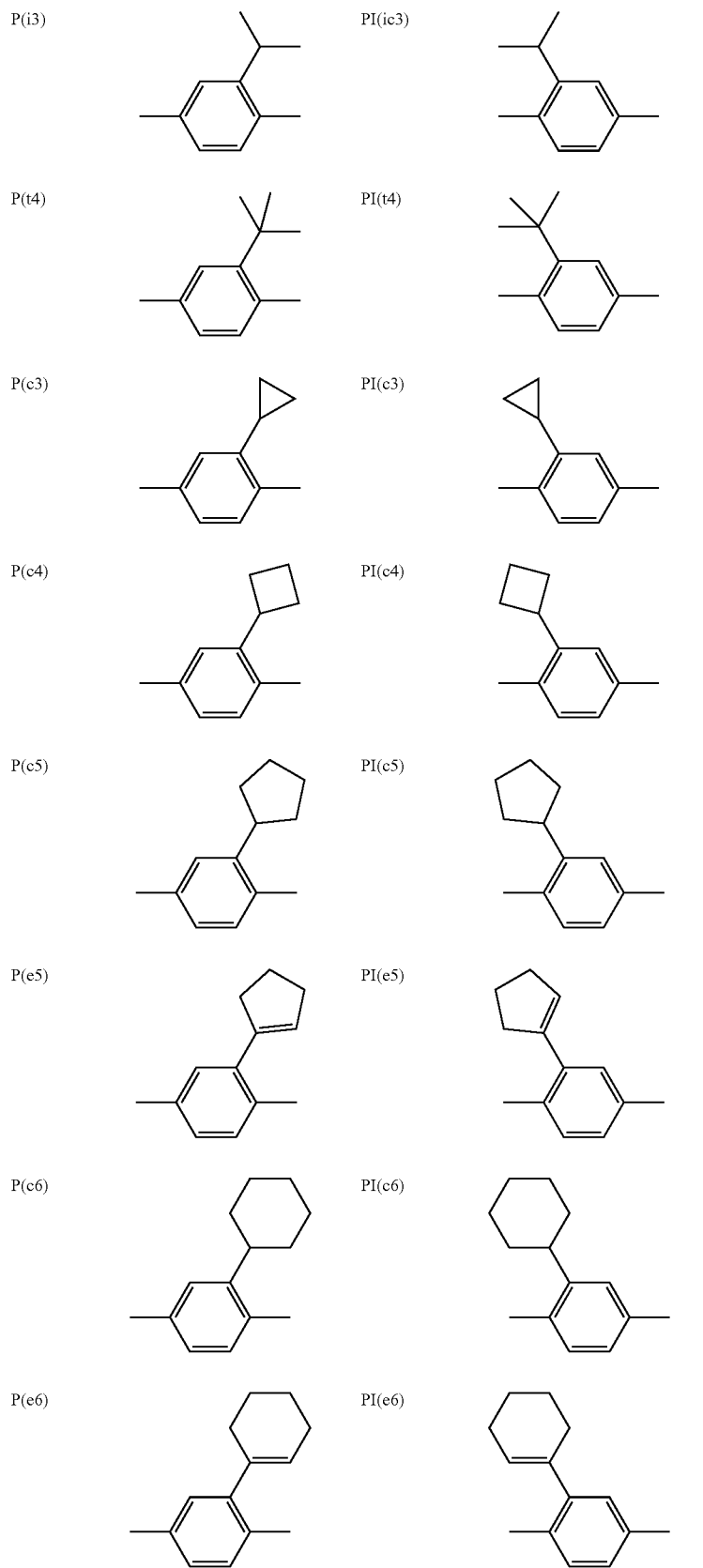

-continued
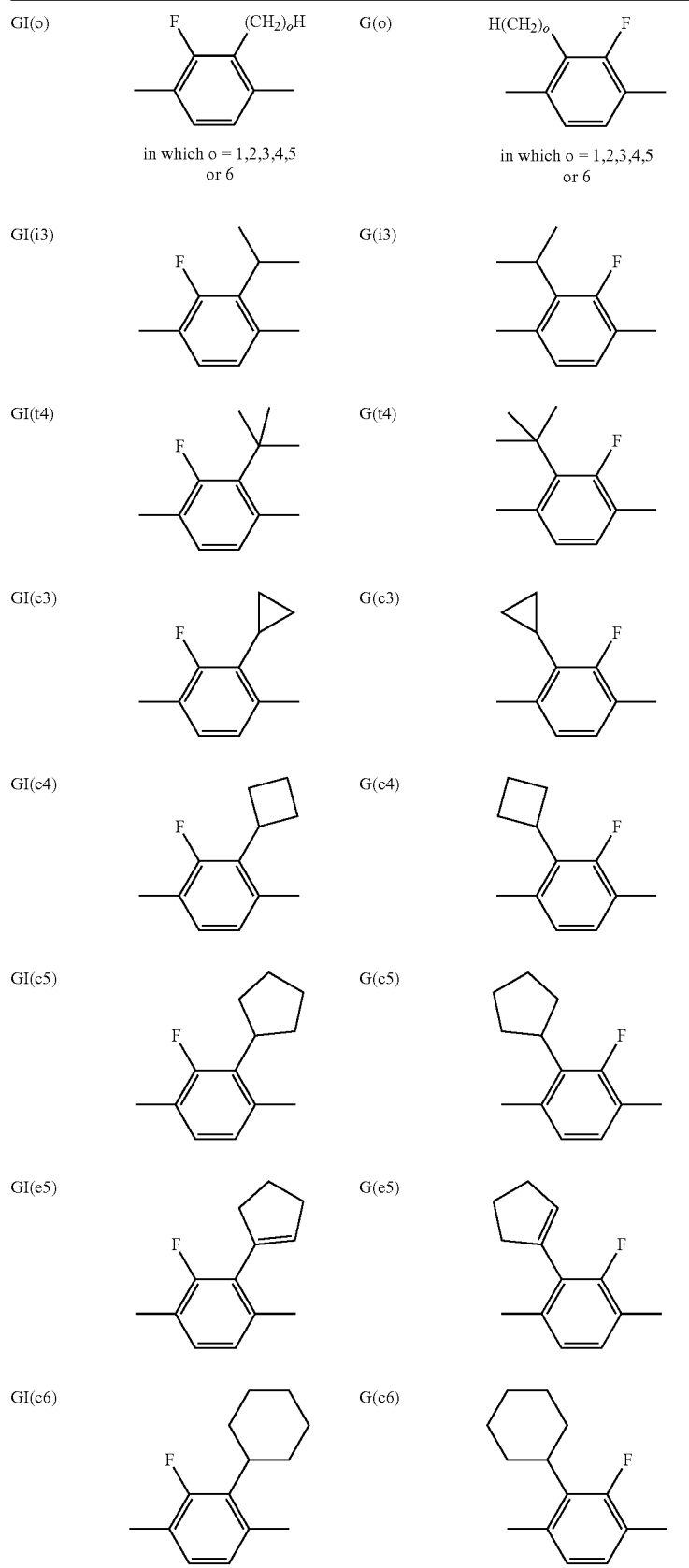

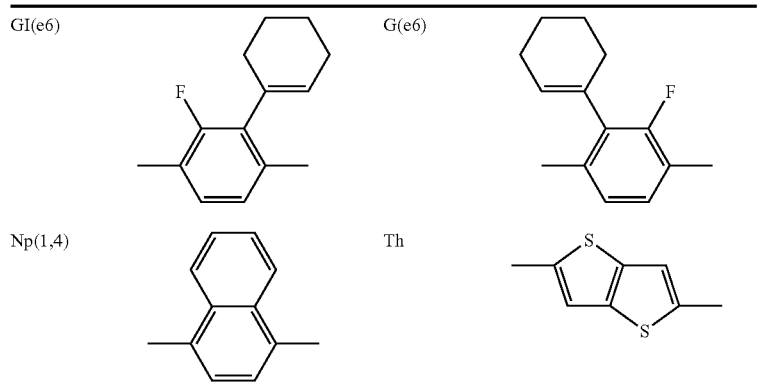

TABLE B

| Linking groups | | | |
|---|---|---|---|
| E | —$CH_2CH_2$— | Z | —CO—O— |
| V | —CH=CH— | ZI | —O—CO— |
| X | —CF=CH— | O | —$CH_2$—O— |
| XI | —CH=CF— | OI | —O—$CH_2$— |
| B | —CF=CF— | Q | —$CF_2$—O— |
| T | —C≡C— | QI | —O—$CF_2$— |
| W | —$CF_2CF_2$— | | |

TABLE B

| End groups | | | |
|---|---|---|---|
| Left-hand side | | Right-hand side | |
| Used alone | | | |
| -n- | $C_nH_{2n+1}$— | -n | —$C_nH_{2n+1}$ |
| -no- | $C_nH_{2n+1}$—O— | -On | —O—$C_nH_{2n+1}$ |
| -V- | $CH_2$=CH— | -V | —CH=$CH_2$ |
| -nV- | $C_nH_{2n+1}$-CH=CH— | -nV | —$C_nH_{2n}$—CH=$CH_2$ |
| -Vn- | $CH_2$=CH—$C_nH_{2n+1}$— | -Vn | —CH=CH—$C_nH_{2n+1}$ |
| -nVm- | $C_nH_{2n+1}$—CH=CH-$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$C_FH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |
| -TO- | $CF_3O$— | -OT | —$OCF_3$ |
| -FXO- | $CF_2$=CH—O— | -OXF | —O—CH=$CF_2$ |
| -A- | H—C≡C- | -A | —C≡C—H |
| -nA- | $C_nH_{2n+1}$—C≡C— | -An | —C≡C—$C_nH_{2n+1}$ |
| -NA- | N≡C—C≡C— | -AN | —C≡C—C≡N |
| -(cn)- | ![cyclopropyl $(CH_2)_{n-2}$] | -(cn) | ![cyclopropyl $(CH_2)_{n-2}$] |
| -(cn)m- | $(CH_2)_{n-2}$—(CH_2)_m— | -m(cn) | —$(CH_2)_m$—$(CH_2)_{n-2}$ |
| Used in combination with others | | | |
| -...A...- | —C≡C— | -...A... | —C≡C— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m each denote integers, and the three dots "..." are placeholders for other abbreviations from this table.

Branched lateral groups are numbered starting from the position next to the ring (1) where the longest chain is seleted, the smaller number indicating the length of the branch and the superscript number in brackets indicates the position of the branch, for example:

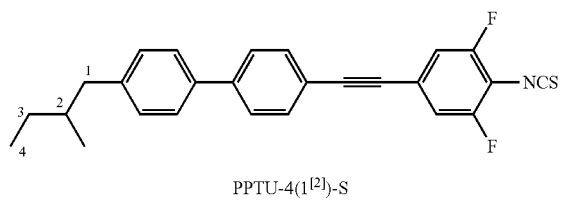

PPTU-4(1[2])-S

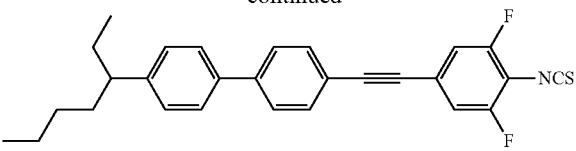

PPTU-5(2[1])-S

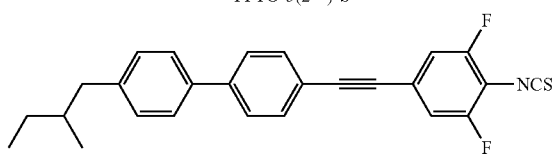

PPTU-4(1[2])-S

The following table shows illustrative structures together with their respective abbreviations. These are shown in order to illustrate the meaning of the rules for the abbreviations. They furthermore represent compounds which are preferably used for mixtures.

TABLE C

Illustrative structures and preferred co-components

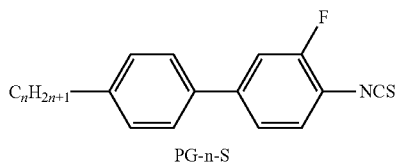

PG-n-S

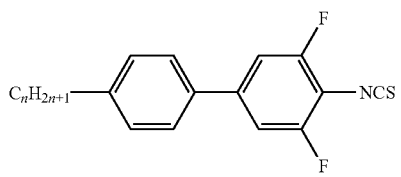

PU-n-S

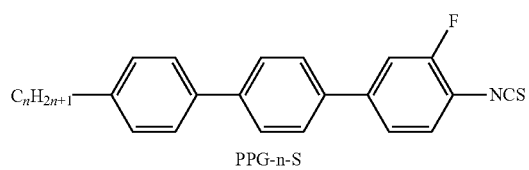

PPG-n-S

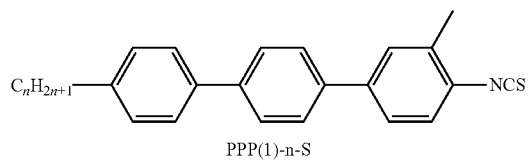

PPP(1)-n-S

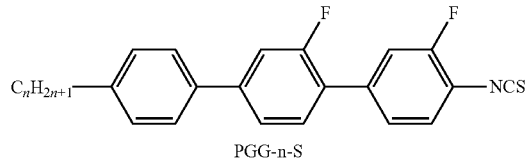

PGG-n-S

TABLE C-continued
Illustrative structures and preferred co-components
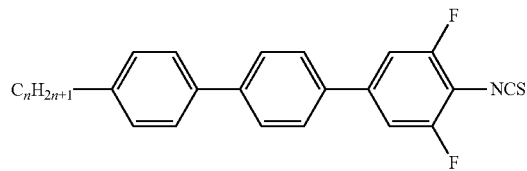
PPU-n-S
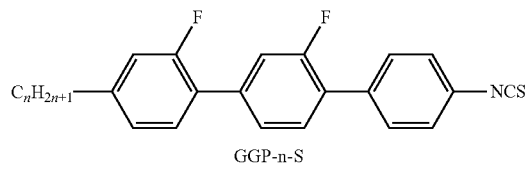
GGP-n-S
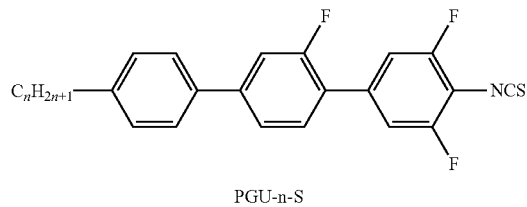
PGU-n-S
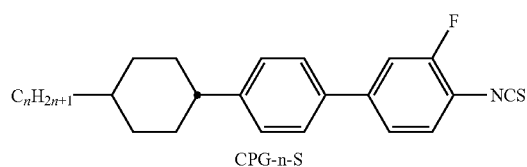
CPG-n-S
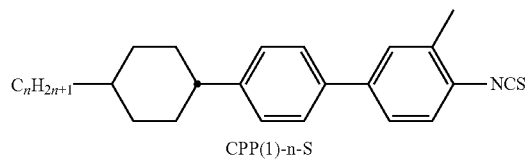
CPP(1)-n-S
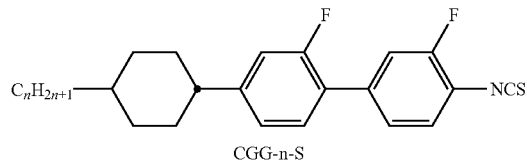
CGG-n-S
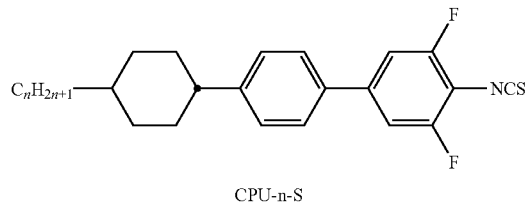
CPU-n-S
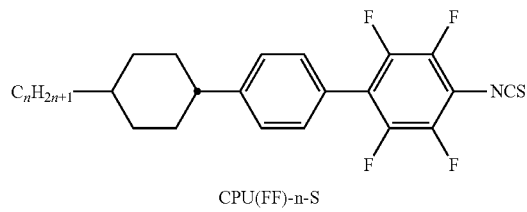
CPU(FF)-n-S TABLE C-continued
Illustrative structures and preferred co-components
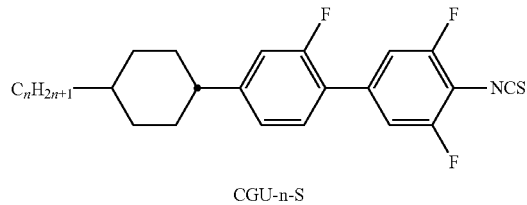
CGU-n-S
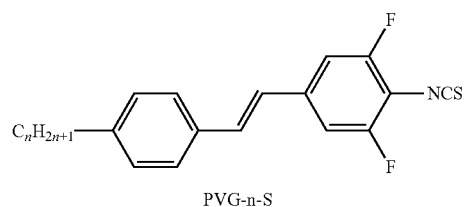
PVG-n-S
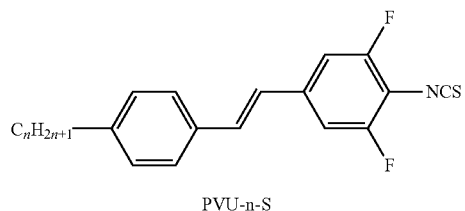
PVU-n-S
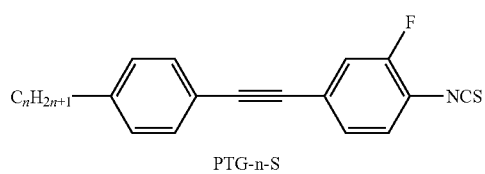
PTG-n-S
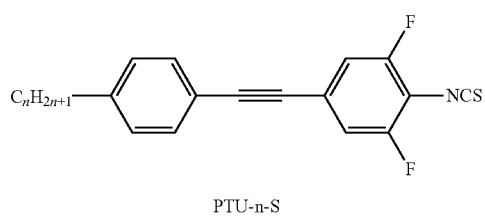
PTU-n-S
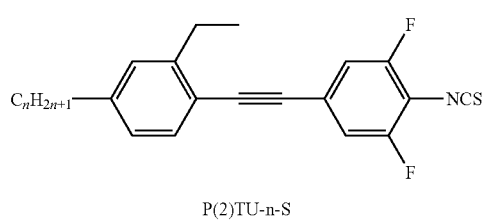
P(2)TU-n-S
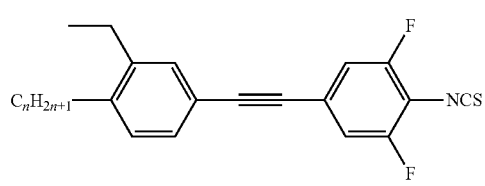
PI(2)TU-n-S TABLE C-continued
Illustrative structures and preferred co-components
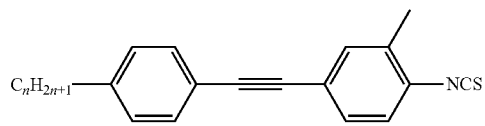
PTP(1)-n-S
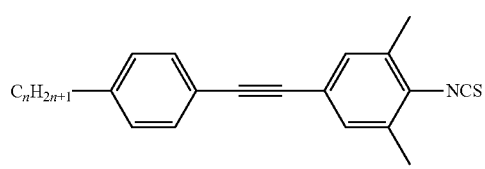
PTP(1,1)-n-S
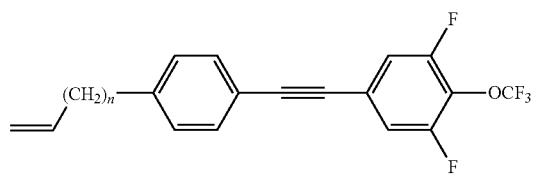
PTU-Vn-OT
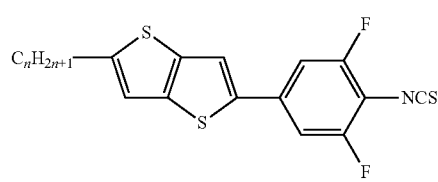
ThU-n-S
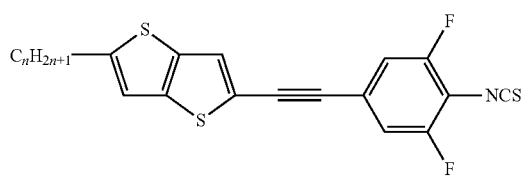
ThTU-n-S
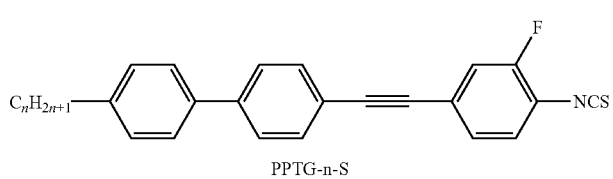
PPTG-n-S
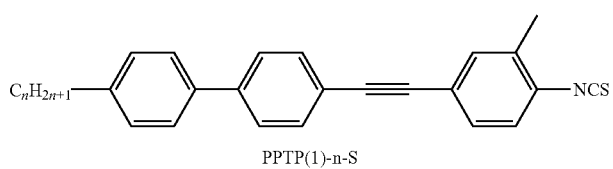
PPTP(1)-n-S
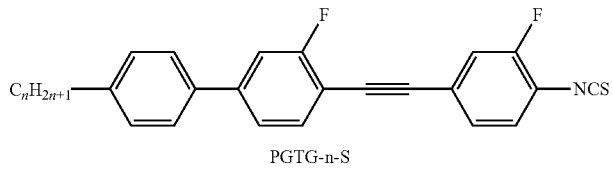
PGTG-n-S TABLE C-continued
Illustrative structures and preferred co-components
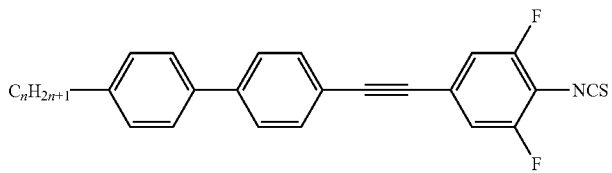
PPTU-n-S
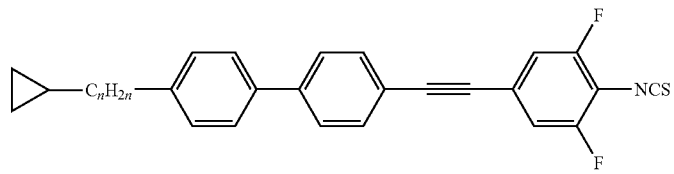
PPTU-(c3)n-S
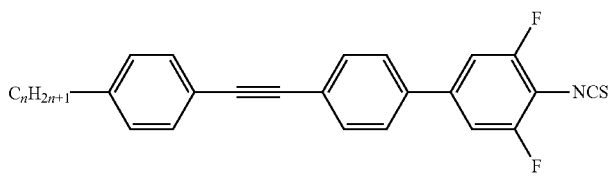
PTPU-n-S
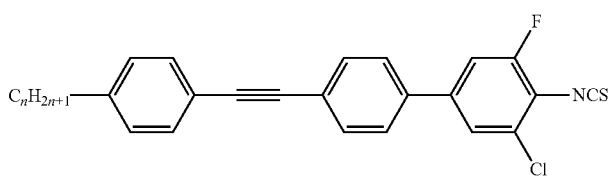
PTPG(Cl)-n-S
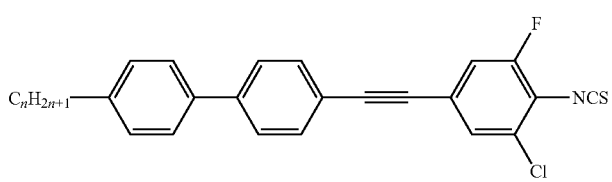
PPTG(Cl)-n-S
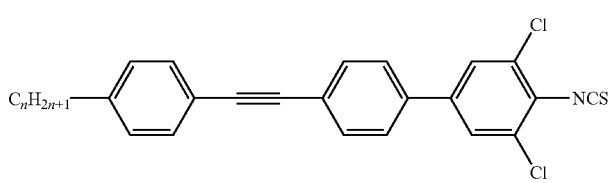
PTPP(Cl,Cl)-n-S
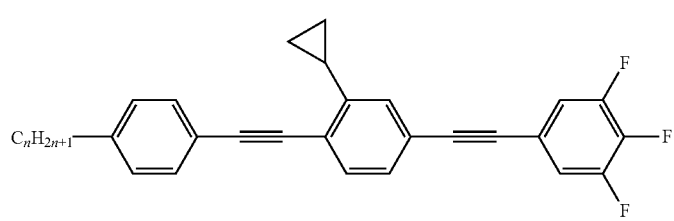
PTPI(c3)TU-n-F TABLE C-continued
Illustrative structures and preferred co-components
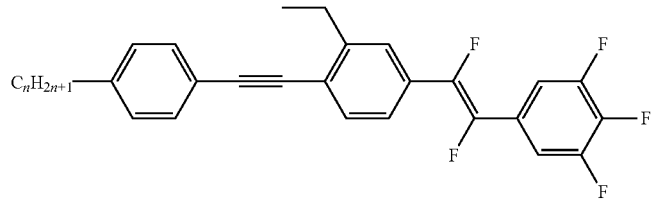
PTPI(2)WU-n-F
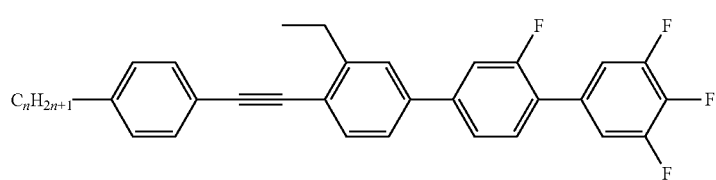
PTPI(2)GU-n-F
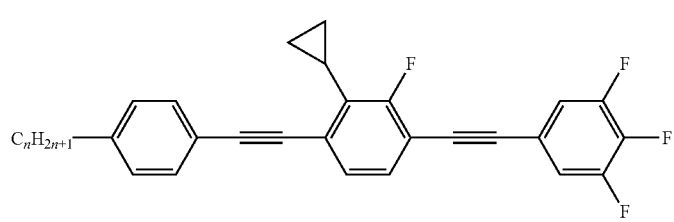
PTG(c3)TU-n-F
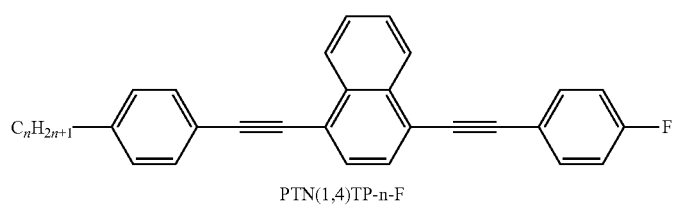
PTN(1,4)TP-n-F
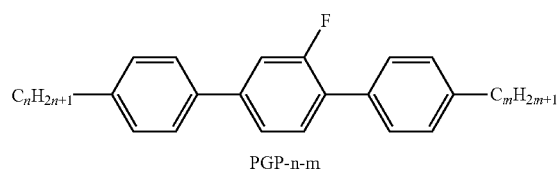
PGP-n-m
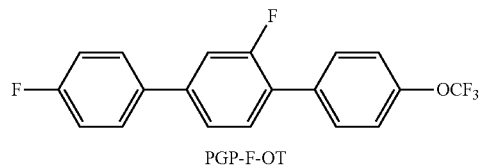 [SMILES: Fc1ccc(-c2ccc(-c3ccc(OC(F)(F)F)cc3)c(F)c2)cc1]
PGP-F-OT
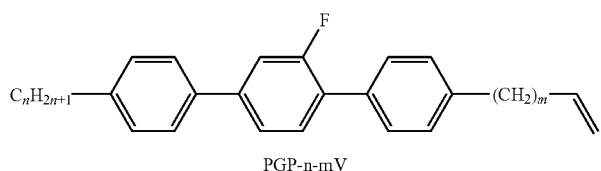
PGP-n-mV TABLE C-continued
Illustrative structures and preferred co-components
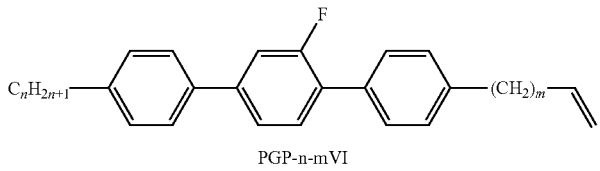
PGP-n-mVI
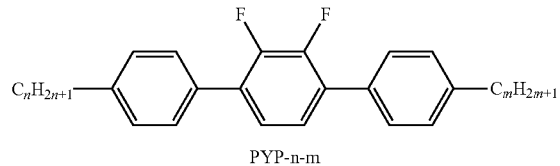
PYP-n-m
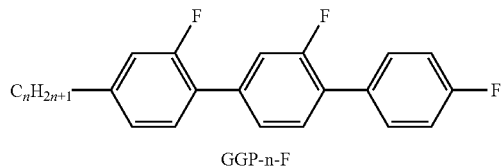
GGP-n-F
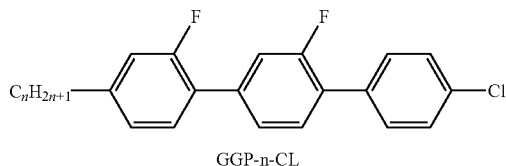
GGP-n-CL
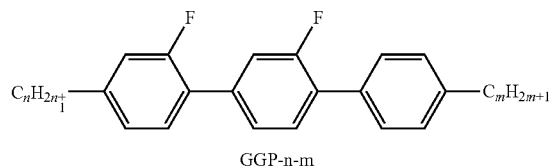
GGP-n-m
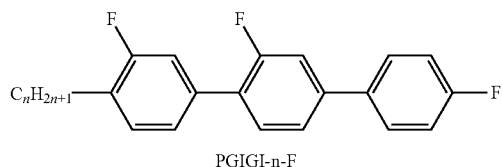
PGIGI-n-F
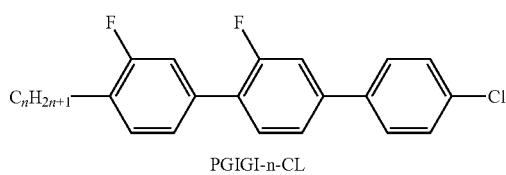
PGIGI-n-CL
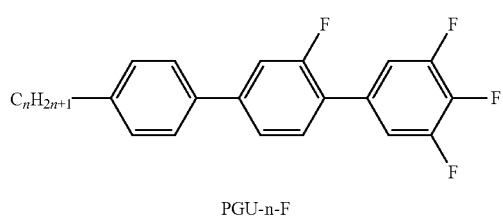
PGU-n-F TABLE C-continued
Illustrative structures and preferred co-components
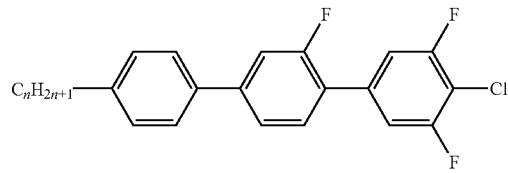
PGU-n-CL
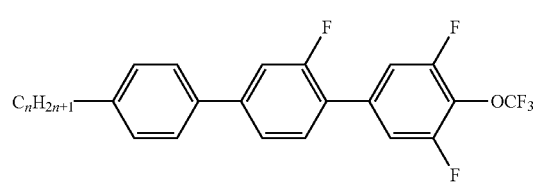
PGU-n-OT
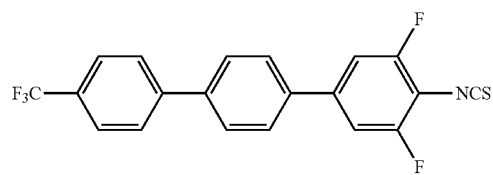
PPU-T-S
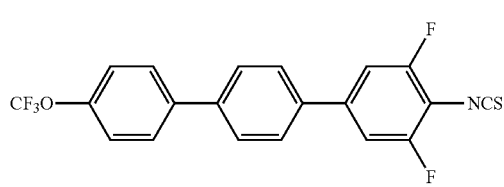
PPU-TO-S
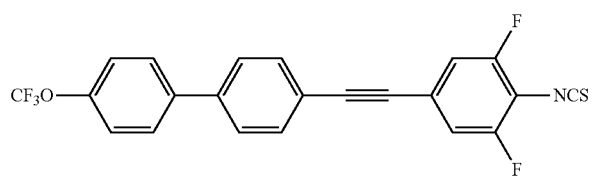
PPTU-TO-S
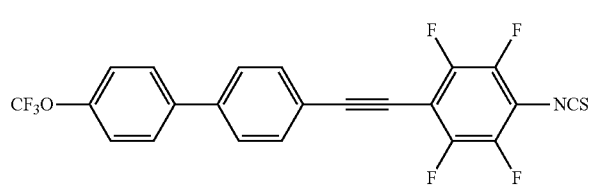
PPTU(FF)-TO-S
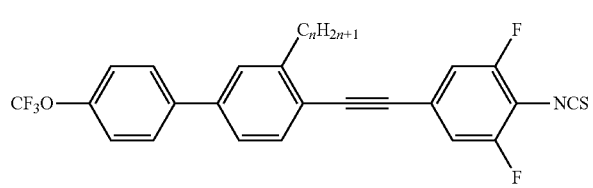
PP(n)TU-TO-S TABLE C-continued Illustrative structures and preferred co-components

PTPU-TO-S

PTPTU-TO-S

PPTUI-n-m

PPTY-n-m

PGGP-n-m

PGIGP-n-m

PGIGP-n-Om

PGIGP-nO-m

TABLE C-continued
Illustrative structures and preferred co-components
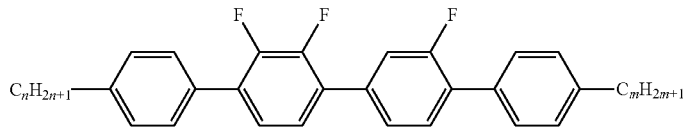
PYGP-n-m
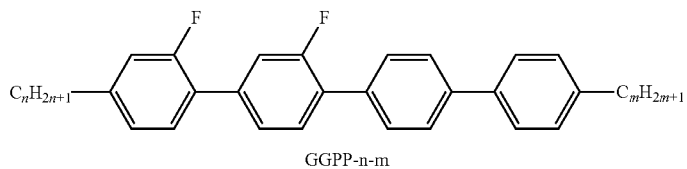
GGPP-n-m
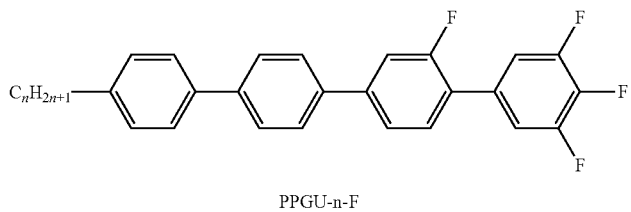
PPGU-n-F
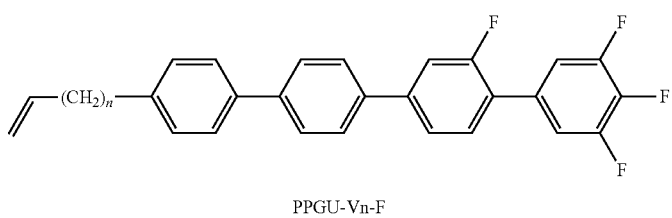
PPGU-Vn-F
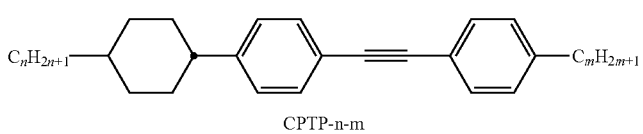
CPTP-n-m
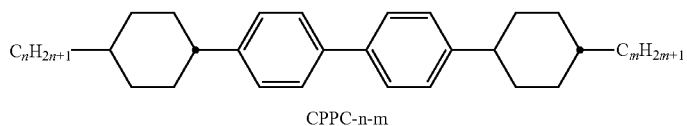
CPPC-n-m
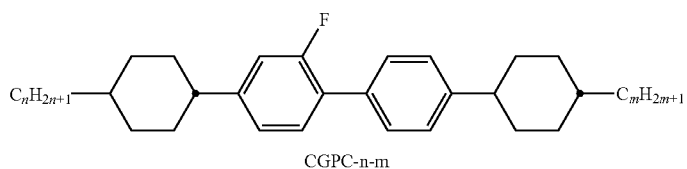
CGPC-n-m
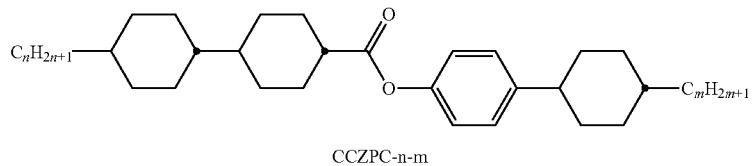
CCZPC-n-m TABLE C-continued
Illustrative structures and preferred co-components
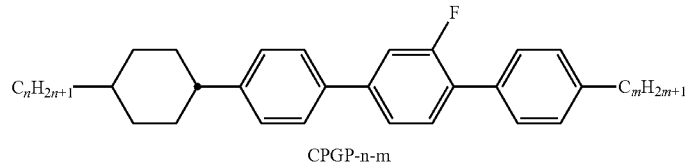
CPGP-n-m
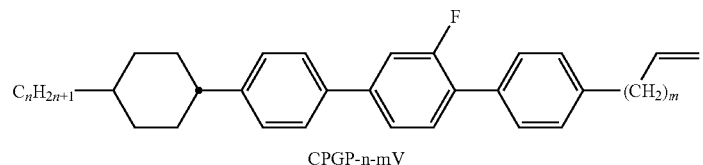
CPGP-n-mV
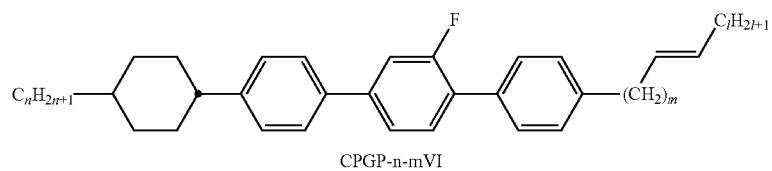
CPGP-n-mVI
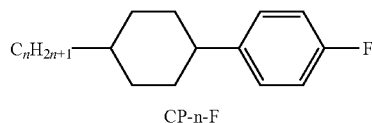
CP-n-F
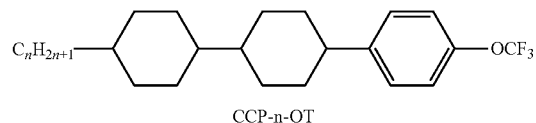
CCP-n-OT
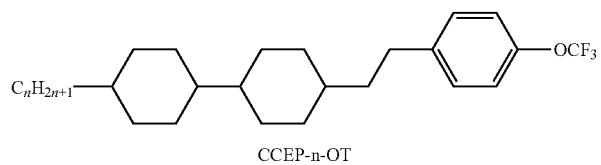
CCEP-n-OT
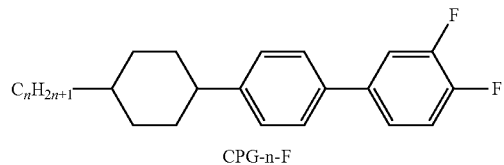
CPG-n-F
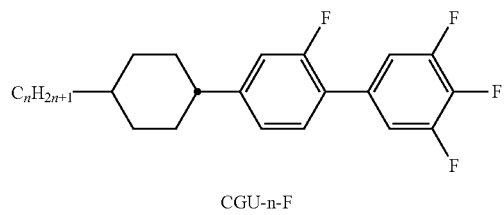
CGU-n-F TABLE C-continued
Illustrative structures and preferred co-components
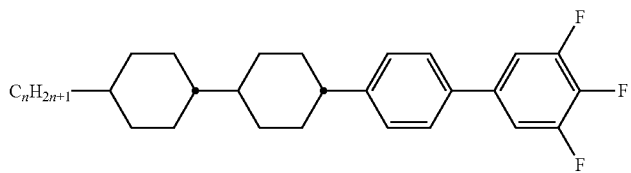
CCPU-n-F
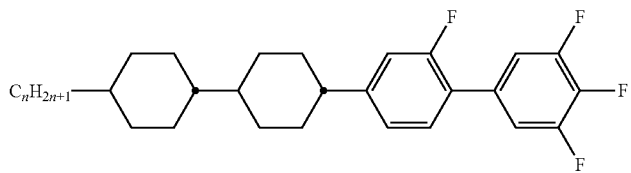
CCGU-n-F
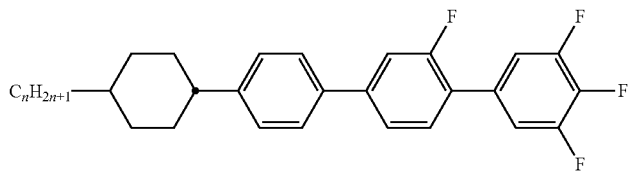
CPGU-n-F
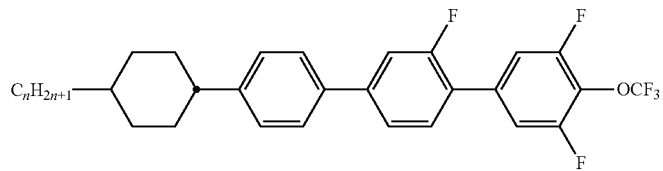
CPGU-n-OT
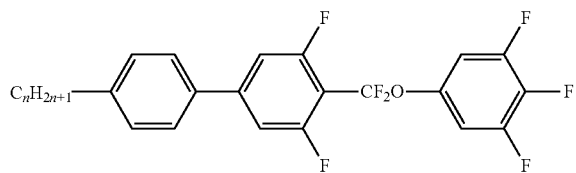
PUQU-n-F
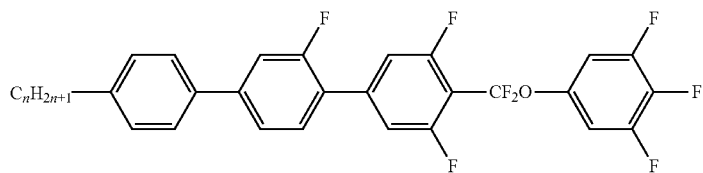
PGUQU-n-F
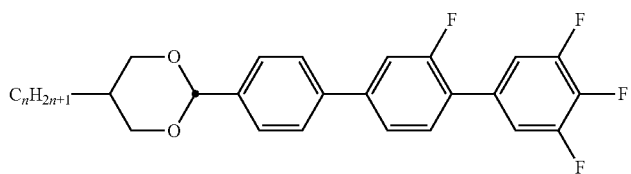
DPGU-n-F

TABLE C-continued

Illustrative structures and preferred co-components

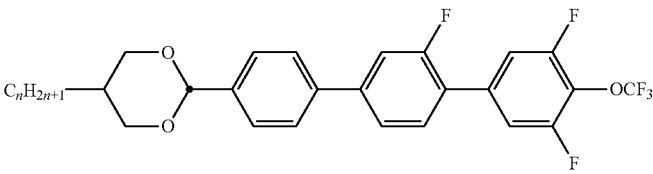

DPGU-n-OT

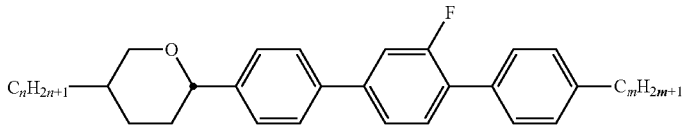

APGP-n-m in which m and n, identically or differnetly, are 1,2,3,4,5,6 or 7.

Preferably, the medium according to the invention comprises one or more compounds selected from the compounds of Table C.

The following table, Table D, shows illustrative compounds which can be used as stabilizers in the mesogenic media in accordance with the present invention. The total concentration of these and similar compounds in the media is preferably 5% or less.

TABLE D

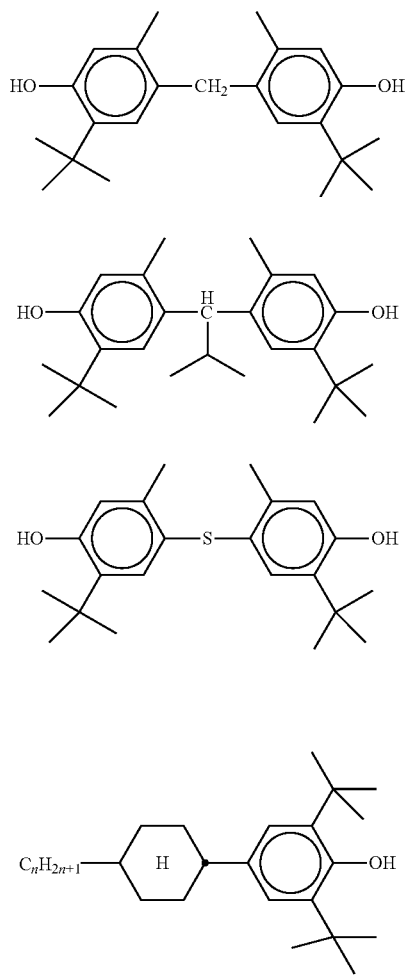

TABLE D-continued
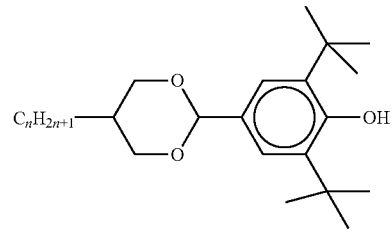
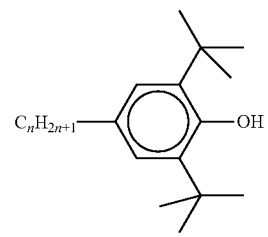
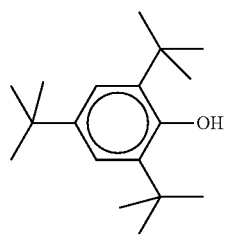
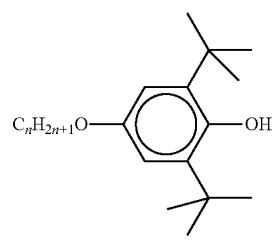
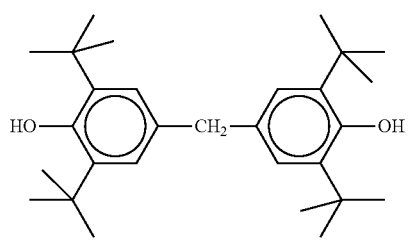
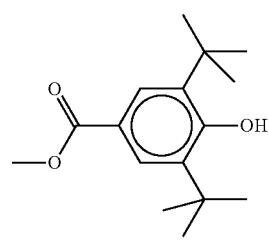

TABLE D-continued
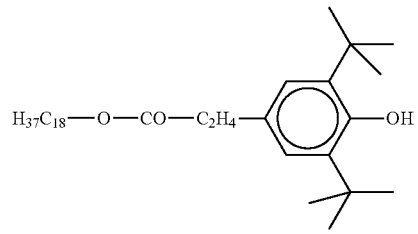
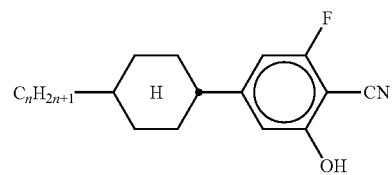
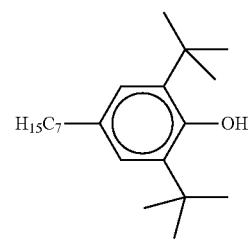
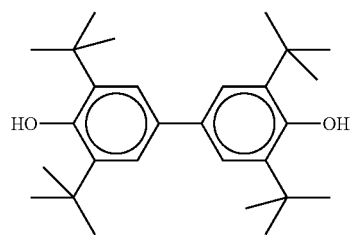
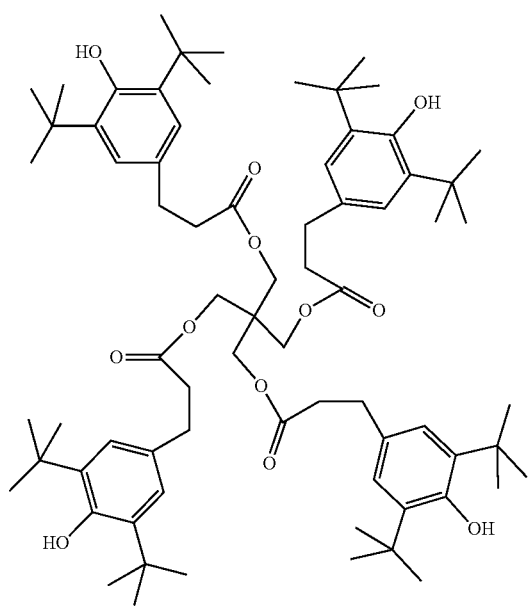 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]

TABLE D-continued
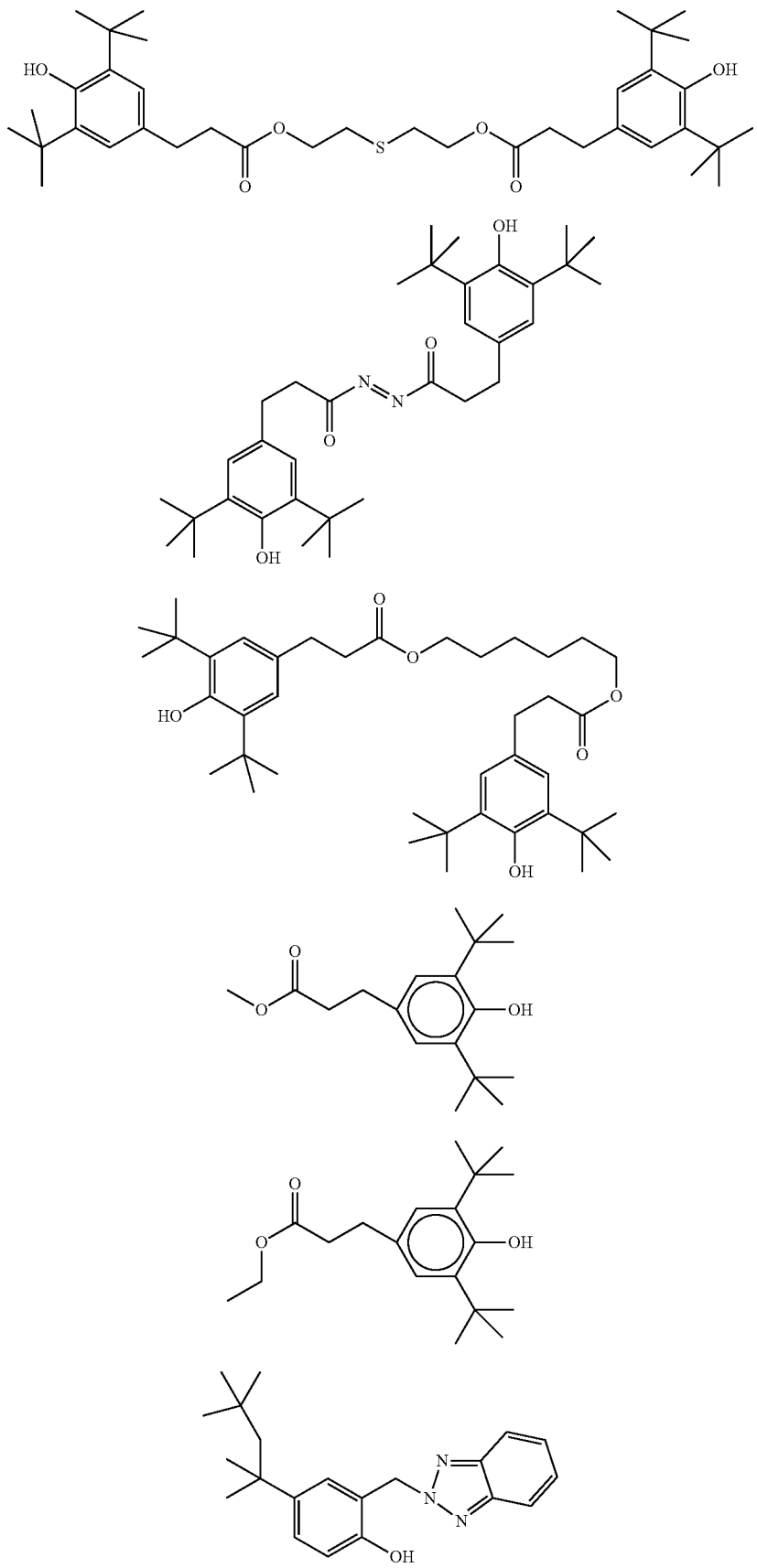

TABLE D-continued
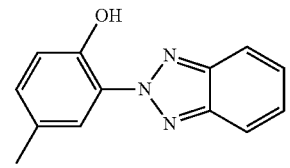 [SMILES: Cc1ccc(O)c(-n2nc3ccccc3n2)c1]
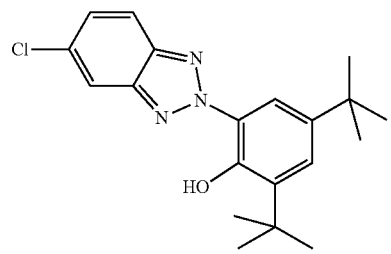 [SMILES: CC(C)(C)c1cc(-n2nc3ccc(Cl)cc3n2)c(O)c(C(C)(C)C)c1]
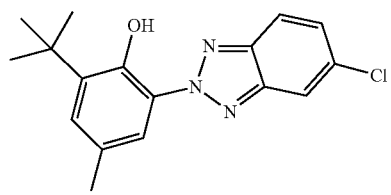 [SMILES: Cc1cc(-n2nc3ccc(Cl)cc3n2)c(O)c(C(C)(C)C)c1]
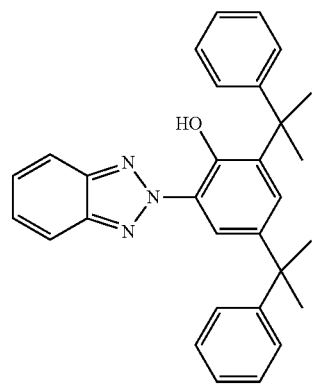 [SMILES: CC(C)(c1ccccc1)c1cc(-n2nc3ccccc3n2)c(O)c(C(C)(C)c2ccccc2)c1]
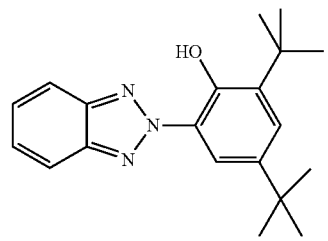 [SMILES: CC(C)(C)c1cc(-n2nc3ccccc3n2)c(O)c(C(C)(C)C)c1]
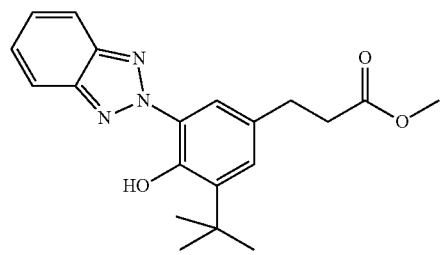 [SMILES: COC(=O)CCc1cc(-n2nc3ccccc3n2)c(O)c(C(C)(C)C)c1]

TABLE D-continued
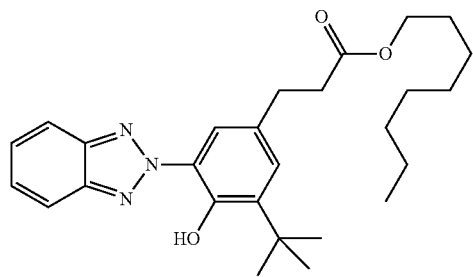 [SMILES: CCCCCCCCOC(=O)CCc1cc(-n2nc3ccccc3n2)c(O)c(C(C)(C)C)c1]
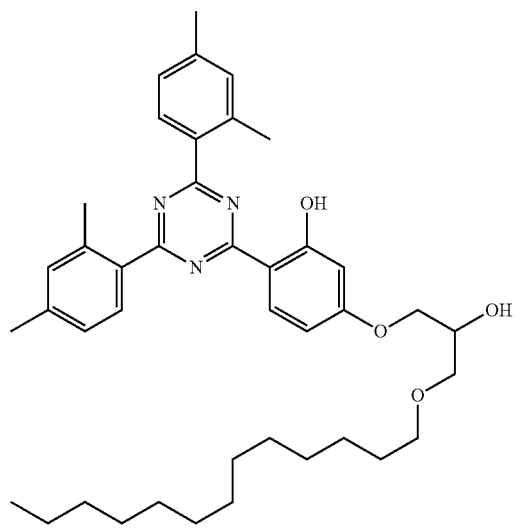 [SMILES: CCCCCCCCCCCCCOCC(O)COc1ccc(-c2nc(-c3ccc(C)cc3C)nc(-c3ccc(C)cc3C)n2)c(O)c1]
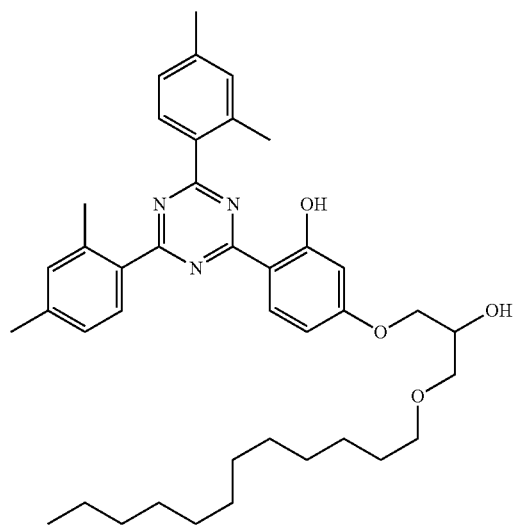 [SMILES: CCCCCCCCCCCCOCC(O)COc1ccc(-c2nc(-c3ccc(C)cc3C)nc(-c3ccc(C)cc3C)n2)c(O)c1]

TABLE D-continued
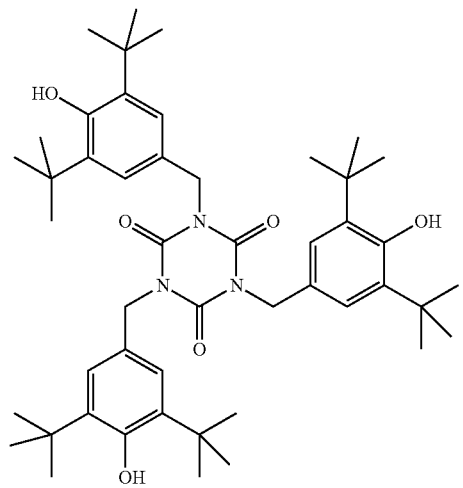 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
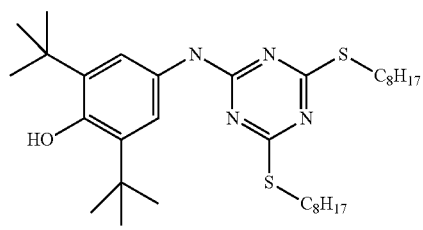
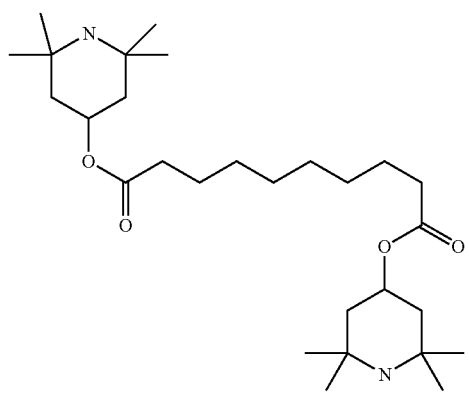
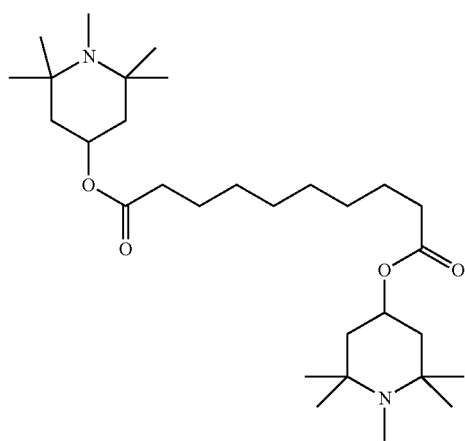

TABLE D-continued
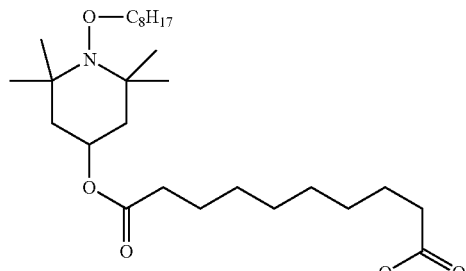
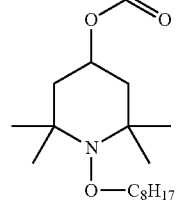
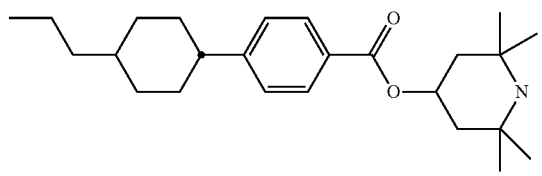
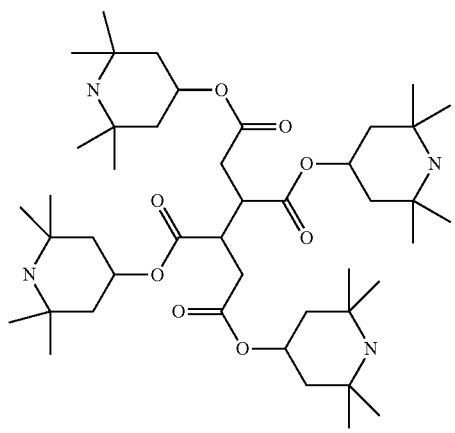
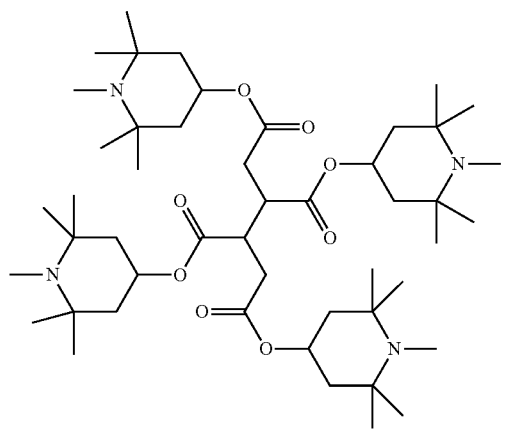

TABLE D-continued

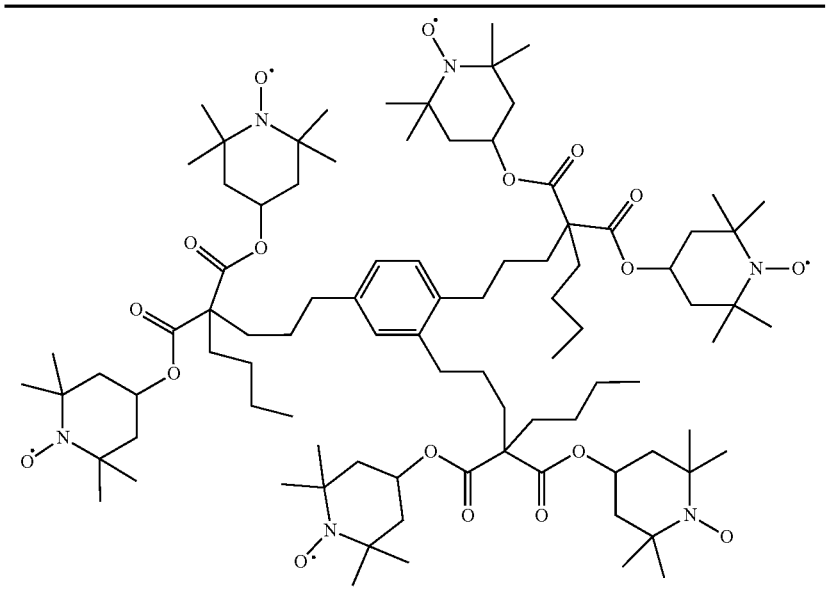

In a preferred embodiment of the present invention, the mesogenic media comprise one or more compounds selected from the group of the compounds from Table D. The following table, Table E, shows illustrative compounds which can preferably be used as chiral dopants in the mesogenic media in accordance with the present invention.

In a preferred embodiment of the present invention, the mesogenic media comprise one or more compounds selected from the group of the compounds of Table E. The mesogenic media in accordance with the present application preferably comprise two or more, preferably four or more, compounds selected from the group consisting of the compounds from the above tables.

Unless indicated otherwise, parts or percent data denote parts by weight or percent by weight.

Above and below:

$V_o$ denotes threshold voltage, capacitive [V] at 20° C.,
$n_e$ denotes extraordinary refractive index at 20° C. and 589 nm,
$n_o$ denotes ordinary refractive index at 20° C. and 589 nm,
$\Delta n$ denotes optical anisotropy at 20° C. and 589 nm,
$\varepsilon_\perp$ denotes dielectric permittivity perpendicular to the director at 20° C. and 1 kHz,
$\varepsilon_\parallel$ denotes dielectric permittivity parallel to the director at 20° C. and 1 kHz,
$\Delta\varepsilon$ denotes dielectric anisotropy at 20° C. and 1 kHz,
m.p. denotes melting point,
cl.p., T(N,I) denotes clearing point [° C.],
$\gamma_1$ denotes rotational viscosity measured at 20° C. [mPa·s],
$K_1$ denotes elastic constant, "splay" deformation at 20° C. [pN],
$K_2$ denotes elastic constant, "twist" deformation at 20° C. [pN],
$K_3$ denotes elastic constant, "bend" deformation at 20° C. [pN],
$K_{avg.}$ denotes average elastic constant defined as $K_{avg.} = \frac{1}{3}(1.5 \cdot K_1 + K_3)$
LTS denotes low-temperature stability (nematic phase), determined in test cells or in the bulk, as specified.

Unless explicitly noted otherwise, all values indicated in the present application for temperatures, such as, for example, the melting point T(C,N), the transition from the smectic (S) to the nematic (N) phase T(S,N) and the clearing point T(N,I) or cl.p., are indicated in degrees Celsius (° C.). M.p. denotes melting point. Furthermore, Tg=glass state, C=crystalline state, N=nematic phase, S=smectic phase and I=isotropic phase. The numbers between these symbols represent the transition temperatures.

The term "threshold voltage" for the present invention relates to the capacitive threshold ($V_o$), also called the Freedericksz threshold, unless explicitly indicated otherwise. In the examples, as is generally usual, the optical threshold can also be indicated for 10% relative contrast ($V_{10}$).

The display used for measurement of the capacitive threshold voltage consists of two plane-parallel glass outer plates at a separation of 20 μm, which each have on the insides an electrode layer and an unrubbed polyimide alignment layer on top, which cause a homeotropic edge alignment of the liquid-crystal molecules.

The so-called "HTP" denotes the helical twisting power of an optically active or chiral substance in an LC medium (in μm). Unless indicated otherwise, the HTP is measured in the commercially available nematic LC host mixture MLD-6260 (Merck KGaA) at a temperature of 20° C.

The Clearing point is measured using the Mettler Thermosystem FP900. The optical anisotropy ($\Delta n$) is measured using an Abbe Refractometer H005 (Natrium-spectral lamp Na10 at 589 nm, 20° C.). The dielectric anisotropy ($\Delta\varepsilon$) is measured using an LCR-30 Meter E4980A/Agilent (G005) at 20° C. (E-parallel-cells with JALS 2096-R1). The turn on voltage ($V_o$) is measured using an LCR-Meter E4980A/Agilent (G005) at 20° C. ($\varepsilon$-parallel-cells with JALS 2096-R1). The rotational viscosity ($\gamma_1$) is measured using a TOYO LCM-2 (0002) at 20° C. (gamma 1 negative cells with JALS-2096-R 1). The elastic constant ($K_1$, splay) is measured using an LCR-Meter E4980A/Agilent (G005) at 20° C. ($\varepsilon$ parallel-cells with JALS 2096-R1). $K_3$: The elastic constant ($K_3$, bend) is measured using an LCR-Meter E4980A/Agilent (G005) at 20° C. ($\varepsilon$-parallel-cells with JALS 2096-R1).

Unless explicitly noted otherwise, all concentrations in the present application are indicated in percent by weight and relate to the corresponding mixture as a whole, comprising all solid or liquid-crystalline components, without solvents. All physical properties are determined in accordance with "Merck Liquid Crystals, Physical Properties of Liquid Crystals", Status November 1997, Merck KGaA, Germany, and apply for a temperature of 20° C., unless explicitly indicated otherwise.

EXAMPLES

The present invention is illustrated in detail by the following non-restrictive working examples.

Synthesis Examples

Abbreviations:
RT Room temperature (typically 20° C.±1° C.),
MTB ether Methyl tertiary-butyl ether,
DCM Dichlormethane.

Synthesis Example 1: 5-[2-[4-[4-(2-Methylbutyl) phenyl]phenyl]ethynyl]-2,1,3-benzothiadiazole

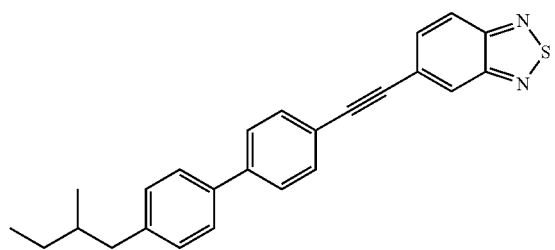 [SMILES: CCC(C)Cc1ccc(-c2ccc(C#Cc3ccc4nsnc4c3)cc2)cc1]

Step 1.1: 1-[4-(4-Bromophenyl)phenyl]-2-methyl-butan-1-one

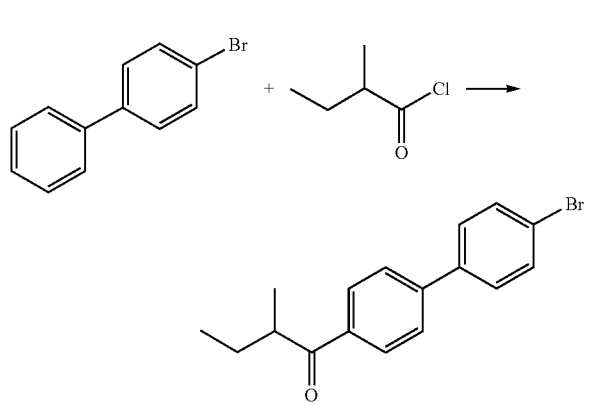

A mixture of 4-bromobiphenyl (25 g, 105 mmol) and 2-methylbutanoyl chloride (15 ml, 120 mmol) in dichloromethane (50 ml), is treated with a mixture of aluminum chloride (16 g, 120 mmol) in dichloromethane (100 ml) at −5° C., and the reaction is stirred for 5 h at −2° C. The reaction mixture is poured onto a mixture of ice and aqueous and extracted (3×) with dichloromethane. Combined organic extracts were dried over magnesium sulfate, filtered and evaporated in vacuo. The crude material is purified by flash chromatography with 1-chlorbutan. The yield is 31.2 g (94%).

Step 1.2: 1-Bromo-4-[4-(2-methylbutyl)phenyl]benzene

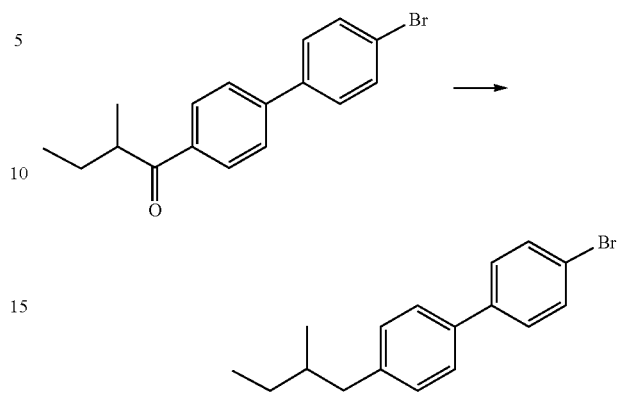

A solution of 1-[4-(4-bromophenyl)phenyl]-2-methyl-butan-1-one (19 g, 59 mmol) in THF (175 ml), is treated with boron trifluoride-diethyl ether complex (75 ml, 597 mmol) at room temperature (exotherm ~30° C.) and added after 10 min. sodium cyanoboro-hydride (23 g, 366 mmol) at 20-35° C., and stirred at 60° C. overnight. The reaction mixture is poured onto a mixture of ice and sodium bicarbonate solution (pH 6-7) and extracted (3×) with MTB ether. Combined organic extracts were dried over magnesium sulfate, filtered and evaporated in vacuo. The yield is 14.6 g (81%).

Step 1.3: Trimethyl-[2-[4-[4-(2-methylbutyl)phenyl]phenyl]ethynyl]silane

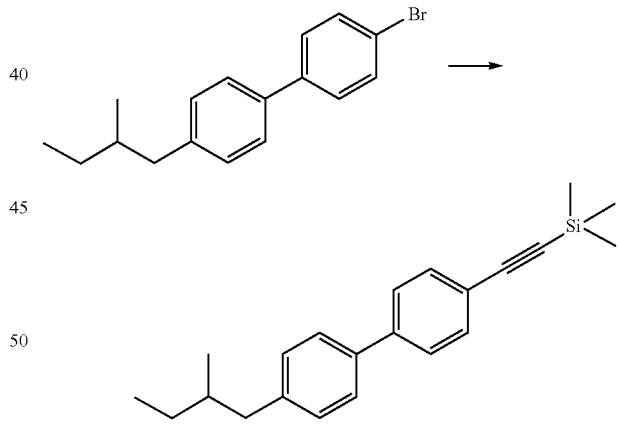

A mixture of 1-bromo-4-[4-(2-methylbutyl)phenyl]benzene (16.6 g, 47 mmol), triethylamine (70 ml), bis(triphenylphosphine)-palladium(II)-chloride (1.4 g, 2 mmol), copper(I)-iodide (220 mg, 1 mmol) and trimethylsilyl acetylene (14 ml, 99 mmol) is heated at reflux temperature overnight. Then water and MTB-ether are added to the reaction mixture. The phases are separated, and the aqueous layer is extracted with MTB-ether. The combined organic phases are washed with dist. water, dried (sodium sulfate) and concentrated i. vac The residue is purified by flash chromatography (heptane) to give trimethyl-[2-[4-[4-(2-methylbutyl)phenyl] phenyl]ethynyl]silane. The yield is 14.7 g (95%).

Step 1.4: 5-[2-[4-[4-(2-Methylbutyl)phenyl]phenyl]ethynyl]-2,1,3-benzothiadiazole

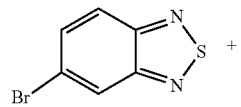 +

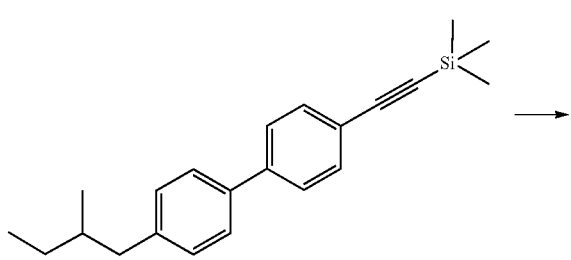

→

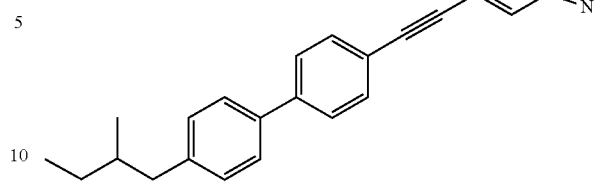

A mixture of trimethyl-[2-[4-[4-(2-methylbutyl)phenyl]phenyl]ethynyl]silane (3.8 g, 11 mmol) and 5-Bromo-2,1,3-benzothiadiazole (CAS-no. 1753-75-9, 2.7 g, 12 mmol) in triemethylamine (25 ml) and DMF(40 ml) and methanol (3 ml) is heated to 70° C. under nitrogen atmosphere. Then tetrakis(triphenylposphin)-palladium (0) (300 mg, 0.26 mmol), potassium carbonate (1.8 g, 13 mmol) are added, and the reaction mixture is stirred at 70° C. overnight. Then it is filtered and concentrated in vacuo. The residue is purified by flash chromatography (heptane and heptane/MTB-ether) to give 5-[2-[4-[4-(2-Methylbutyl)phenyl]phenyl]ethynyl]-2,1,3-benzothiadiazole. The yield is 4.2 g (94%).

Phases: K 109 SmA 115 N 151 I

Δε 6.8

Δn 0.43

In analogy to Synthesis Example 1 the following compounds are obtained:

| No | Compound | Physical parameters |
|---|---|---|
| 1 | | |
| 2 | | |
| 3 | | |
| 4 | | |

| No | Compound | Physical parameters |
|---|---|---|
| 5 | | |
| 6 | | |
| 7 | | |

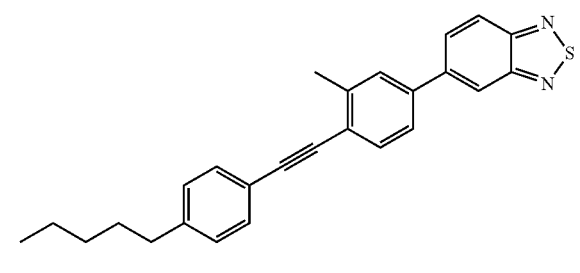 [SMILES: CCCCCc1ccc(C#Cc2ccc(-c3ccc4nsnc4c3)cc2C)cc1]

Synthesis Example 2: 5-[3-Methyl-4-[2-(4-pentylphenyethynyl]phenyl]-2,1,3-benzothiadiazole Step 2.1: 4-Bromo-2-methyl-1-[2-(4-pentylphenyethynyl]benzene

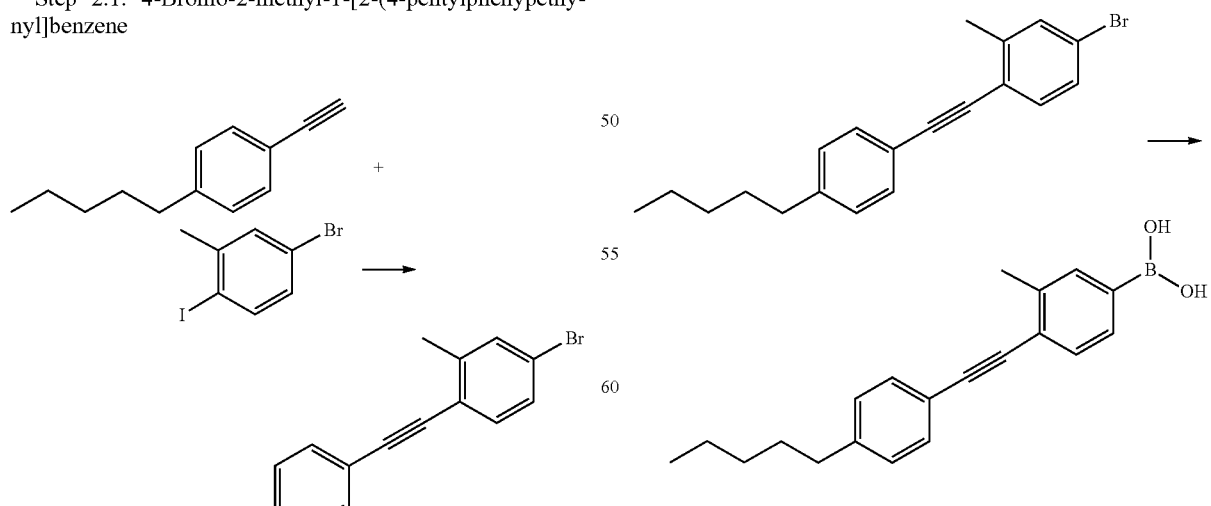

A solution of 1-ethynyl-4-pentyl-benzene (CAS-no. 79887-10-8, 9.4 g, 53 mmol), 4-bromo-1-iodo-2-methyl-benzene(CAS-no. 167858-55-1, 16 g, 53 mmol) and triethylamine (150 ml) is heated at 35° C. temperature. Copper (I)iodide (200 mg, 1 mmol)), 2-dicyclohexylphosphino-2'4'6'-triisopropyl-1,1'-biphenyl (22 mg) and bis(triphenylphosphine)-palladium (II)-chloride (750 mg 1 mmol) are added, and the reaction mixture is stirred at 80° C. overnight. Then it is cooled to RT, filtered and concentrated in vacuo. The residue is purified by silica gel chromatography (heptane/MTB ether 5/1) 35 and crystallization (heptane) to 4-bromo-2-methyl-1-[2-(4-pentylphenyl)ethynyl]benzene. The yield is 18.6 g (99%).

Step 2.2: [3-Methyl-4-[2-(4-pentylphenyl)ethynyl]phenyl]boronic acid

Buthyllithium (37 mL, 15% in n-hexane, 59 mmol) is slowly added to a solution of 4-bromo-2-methyl-1-[2-(4-pentylphenyl)ethynyl]benzene (18.6 g, 53 mmol) in THF (150 mL) at −65° C. under nitrogen atmosphere. The mixture is stirred for 1 h, then a solution of trimethyl borate (CAS 121-43-7) (6.6 ml, 59 mmol) in THF (15 mL) is slowly added. The reaction mixture is stirred for 1 h, then it is allowed to warm up to 5° C. The reaction mixture is quenched with dist. water and acidified with hydrochloric acid (2 M). The aqueous phase is separated and extracted with MTB ether. The combined organic phases are washed with brine, dried (sodium sulphate) and concentrated in vacuo. The residue is suspended in n-heptane, heated up to 50° C., cooled down to 5° C. and filtered in vacuo to give [3-methyl-4-[2-(4-pentylphenyl)ethynyl]phenyl]boronic acid as a colorless solid. The yield is 16 g (71%).

Step 2.3; 5-[3-Methyl-4-[2-(4-pentylphenyethynyl]phenyl]-2,1,3-benzothiadiazole

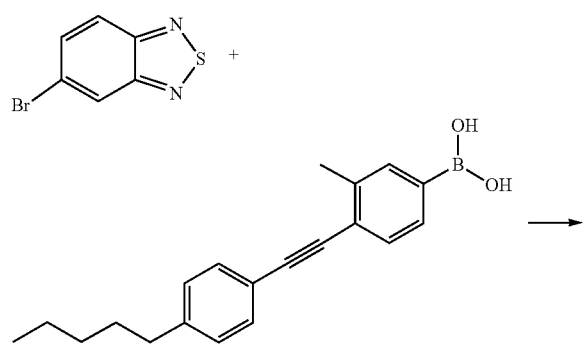

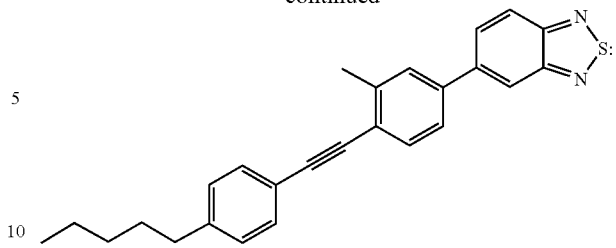

A solution of [3-Methyl-4-[2-(4-pentylphenyl)ethynyl]phenyl]boronic acid (4.7 g, 15 mmol) and 5-Bromo-2,1,3-benzothiadiazole (CAS-no. 1753-75-9, 3 g, 14 mmol) in propanol (30 mL), toluol (25 ml), water (7 ml) and PdCl$_2$(PPh$_3$)$_2$ (300 mg, 427 mmol) is added. The mixture is heated to reflux temperature, followed by dropwise addition of sodium carbonate (4.5 g, 42 mmol). The reaction mixture is stirred for 2 h at reflux temperature (110° C.). It is then cooled to RT, treated with acetic acid (glacial, 1.6 mL) and diluted with MTB ether. The aqueous phase is separated and extracted with MTB ether. The combined organic phases are washed with brine, dried (sodium sulfate) and concentrated in vacuo. The residue is purified by silica gel chromatography (n-heptane and MTB ether) to give 5-[3-Methyl-4-[2-(4-pentylphenyethynyl]phenyl]-2,1,3-benzothiadiazole as a light yellow solid. The yield is 4.8 g (86%).

Phases: K 101 N 125 I
Δε 6.9
Δn 0.42

In analogy to Synthesis Example 2 the following compounds are obtained:

| No | Compound | Physical parameters |
|---|---|---|
| 8 | 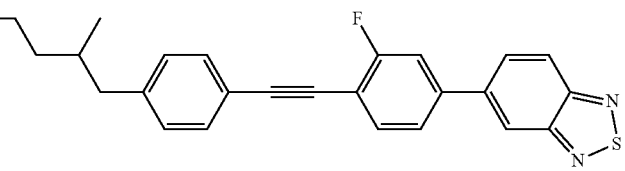 | |
| 9 | 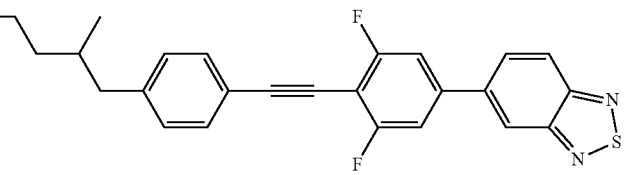 | |
| 10 | 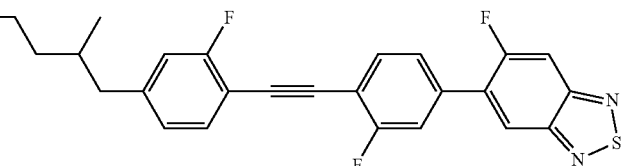 | |
| 11 | 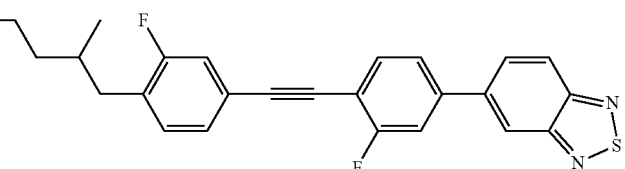 | |

| No | Compound | Physical parameters |
|---|---|---|
| 12 | 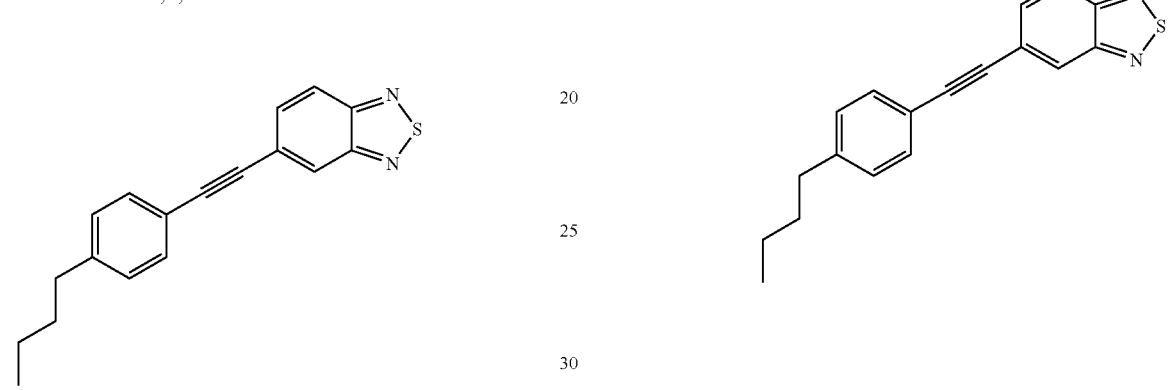 | |

Synthesis Example 3: 5-[2-(4-butylphenypethynyl]-2,1,3-benzothiadiazole

Step 3.1; 5-[2-(4-butylphenypethynyl]-2,1,3-benzothiadiazole

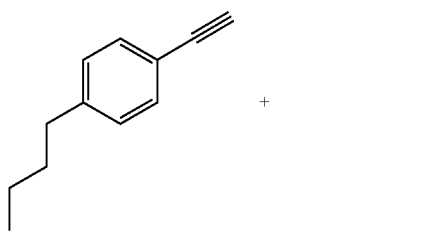

A solution of 1-butyl-4-ethynyl-benzene(CAS-no. 79887-09-5, 4.3 g, 27 mmol), 5-Bromo-2,1,3-benzothiadiazole (CAS-no. 1753-75-9, 6.1 g, 27 mmol) and diisopropylamine (64 mL) in THF (48 mL) is heated slightly below reflux temperature. Copper(I)iodide (5.1 mg, 27 mmol), XPhos (26 mg, 54 mmol) and XPhos Pd G2 (43 mg, 54 mmol) are added, and the reaction mixture is stirred at reflux temperature overnight. Then it is cooled down to RT, filtered and concentrated in vacuo. The residue is purified by silica gel chromatography (n-heptane and 1-chlorobutane) to give 5-[2-(4-butylphenypethynyl]-2,1,3-benzothiadiazole. As a light yellow solid. The yield is 5.2 g (65%).

m.p.: 86° C.
Δε 6.1
Δn 0.32

In analogy to Synthesis Example 3 the following compounds are obtained:

| No | Compound | Physical parameters |
|---|---|---|
| 13 | | |

| No | Compound | Physical parameters |
|---|---|---|
| 14 | 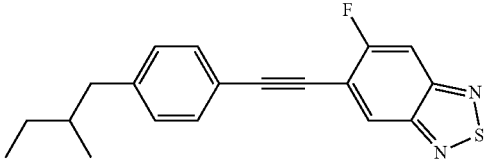 [SMILES: CCC(C)Cc1ccc(C#Cc2cc3nsnc3cc2F)cc1] | m.p.: 54° C.<br>Δε 2.7<br>Δn 0.27 |
| 15 | 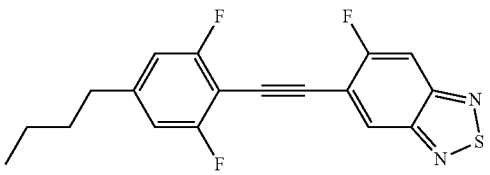 [SMILES: CCCCc1cc(F)c(C#Cc2cc3nsnc3cc2F)c(F)c1] | |
| 16 | 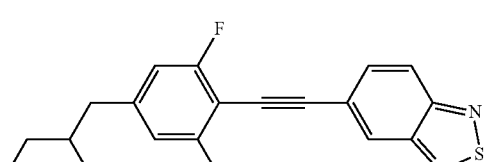 | |
| 17 | 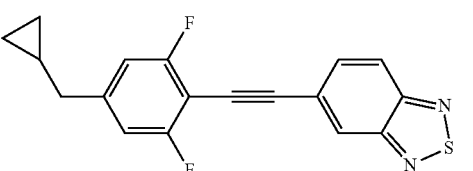 | |
| 18 | 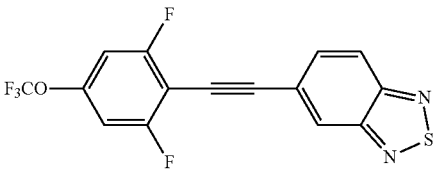 | |
| 19 | 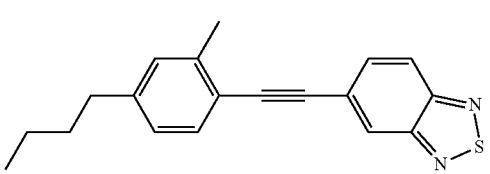 | m.p.: 82° C.<br>Δε 2.6<br>Δn 0.22 |
| 19 | 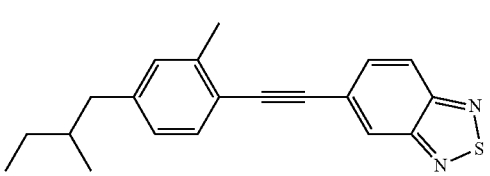 [SMILES: CCC(C)Cc1ccc(C#Cc2ccc3nsnc3c2)c(C)c1] | |
| 20 | 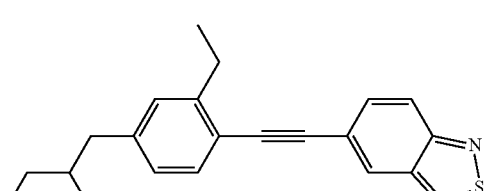 | |

| No | Compound | Physical parameters |
|---|---|---|
| 21 | 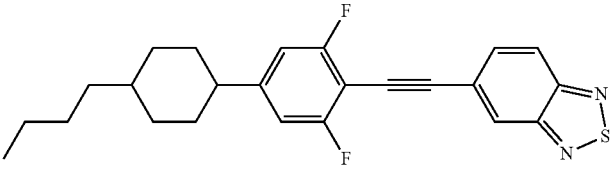 [SMILES: CCCCC1CCC(c2cc(F)c(C#Cc3ccc4nsnc4c3)c(F)c2)CC1] | |

Synthesis Example 4: 5-[4-(4-Propylcyclohexyl)phenyl]-2,1,3-benzothiadiazole

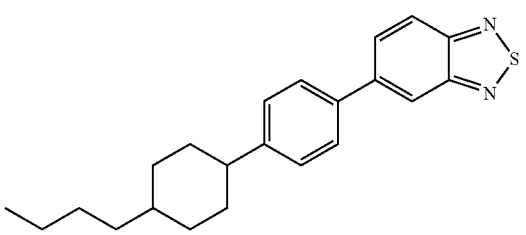 [SMILES: CCCCC1CCC(c2ccc(-c3ccc4nsnc4c3)cc2)CC1]

Step 4.1: 5-[4-(4-propylcyclohexyl)phenyl]-2,1,3-benzothiadiazole

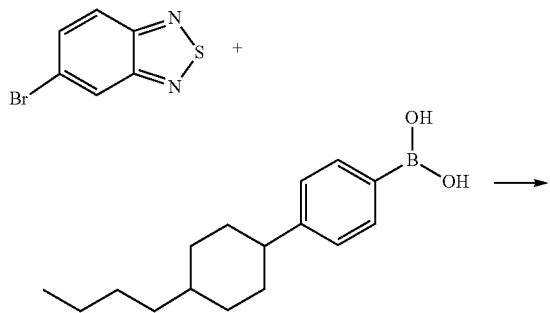

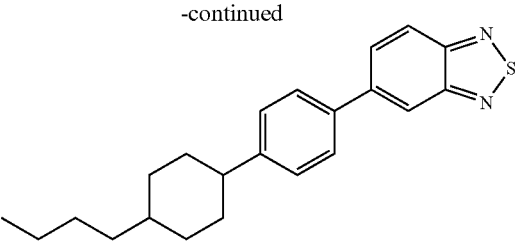

A solution of [4-(4-Propylcyclohexyl)phenyl]boronic acid (CAS-no; 156837-90-0, 4.8 g, 18 mmol) and 5-Bromo-2,1,3-benzothiadiazole (CAS-no. 1753-75-9, 4 g, 17 mmol) in propanol (8 mL), toluol (27 ml), water (8 ml) and PdCl$_2$(PPh$_3$)$_2$ (360 mg, 514 mmol) is added. The mixture is heated to reflux temperature, followed by dropwise addition of sodium carbonate (5,6 g, 4253 mmol). The reaction mixture is stirred for 2 h at reflux temperature (110° C.). It is then cooled to RT, treated with acetic acid (glacial, 1.6 mL) and diluted with MTB ether. The aqueous phase is separated and extracted with MTB ether. The combined organic phases are washed with brine, dried (sodium sulfate) and concentrated in vacuo. The residue is purified by silica gel chromatography (n-heptane and MTB ether) to 5-[4-(4-propylcyclohexyl)phenyl]-2,1,3-benzothiadiazole as a light yellow solid. The yield is 4.3 g (69%).

Phases: K 89 N 146 I

Δε 5.8

Δn 0.23

In analogy to Synthesis Example 4 the following compounds are obtained:

| No | Compound | Physical parameters |
|---|---|---|
| 21 | 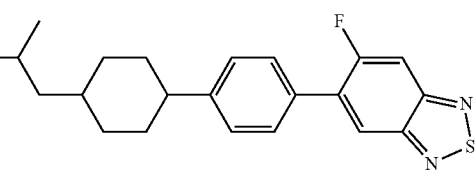 | |
| 22 | 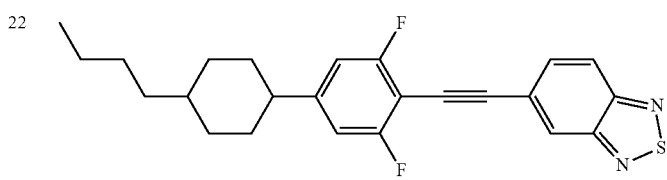 | |

| No | Compound | Physical parameters |
|---|---|---|
| 23 | 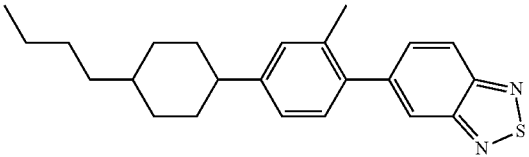 [SMILES: CCCCC1CCC(c2ccc(-c3ccc4nsnc4c3)c(C)c2)CC1] | |
| 24 | 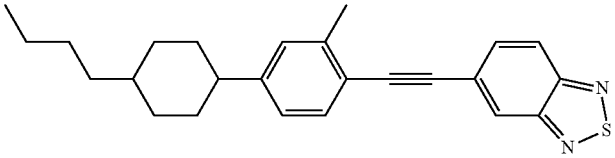 [SMILES: CCCCC1CCC(c2ccc(C#Cc3ccc4nsnc4c3)c(C)c2)CC1] | |

Mixture Examples

The following mixtures H1 and H2 are prepared as a base mixture to which the heterocyclic compounds of formula I are added.

The following abbreviations for compounds are used:
StabiD

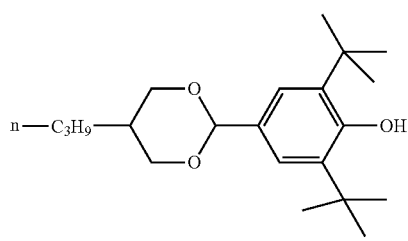

The following mixture H1 is prepared as a base mixture to which the heterocyclic compounds of formula I are added.

| Base mixture H1 | | | |
|---|---|---|---|
| Compounds | % | Properties | |
| StabiD | 0.12 | Clearing point [° C.]: | 151 |
| PTU-3-S | 15.98 | Δn [589 nm, 20° C.]: | 0.3779 |
| PGU-3-S | 13.98 | Δε [1 kHz, 20° C.]: | 22.7 |
| PPTU-5-S | 19.98 | $\gamma_1$ [mPa s, 20° C.]: | 384 |
| CPU-2-S | 34.96 | $\varepsilon_{r, \parallel}$ [20° C., 19 GHz]: | 3.59 |
| CPU-4-S | 14.98 | tan $\delta_{\varepsilon\ r, \parallel}$ [20° C., 19 GHz]: | 0.0059 |
| Σ | 100.0 | $\varepsilon_{r, \perp}$ [20° C., 19 GHz]: | 2.47 |
| | | tan $\delta_{\varepsilon\ r, \perp}$ [20° C., 19 GHz]: | 0.0106 |
| | | τ [20° C., 19 GHz]: | 0.311 |
| | | η [20° C., 19 GHz]: | 29.3 |

| Base mixture H2 | | | |
|---|---|---|---|
| Compound | % | Properties | |
| BCH-3F•F | 12.0 | Clearing point [° C.]: | 92.5 |
| BCH-5F•F | 10.0 | Δn [589 nm, 20° C.]: | 0.0969 |
| ECCP-30CF3 | 5.0 | Δε [1 kHz, 20° C.]: | 5.3 |
| ECCP-50CF3 | 5.0 | $\varepsilon_{r, \parallel}$ [20° C., 19 GHz]: | 2.49 |
| CBC-33F | 2.0 | tan $\delta_{\varepsilon\ r, \parallel}$ [20° C., 19 GHz]: | 0.0049 |
| CBC-53F | 2.0 | $\varepsilon_{r, \perp}$ [20° C., 19 GHz]: | 2.24 |
| CBC-55F | 2.0 | tan $\delta_{\varepsilon\ r, \perp}$ [20° C., 19 GHz]: | 0.0125 |
| PCH-6F | 8.0 | τ [20° C., 19 GHz]: | 0.100 |
| PCH-7F | 6.0 | η [20° C., 19 GHz]: | 8.0 |
| CCP-20CF3 | 8.0 | | |
| CCP-30CF3 | 12.0 | | |
| CCP-40CF3 | 7.0 | | |
| CCP-50CF3 | 11.0 | | |
| PCH-5F | 10.0 | | |
| Σ | 100 | | |

Mixture Example M1

The medium M1 consists of 90% of host H1 and 10% of compound of Synthesis Example 1.

| Compounds | % | Properties | |
|---|---|---|---|
| Compound Ex. 1, | 10.0 | Clearing point [° C.]: | 149 |
| Base mixture H1 | 90.0 | $\varepsilon_{r,\parallel}$ [20° C., 19 GHz]: | 3.57 |
| Σ | 100 | tan $\delta\varepsilon_{r,\parallel}$ [20° C., 19 GHz]: | 0.0053 |
| | | $\varepsilon_{r,\perp}$ [20° C., 19 GHz]: | 2.45 |
| | | tan $\delta\varepsilon_{r,\perp}$ [20° C., 19 GHz]: | 0.0094 |
| | | τ [20° C., 19 GHz]: | 0.313 |
| | | η [20° C., 19 GHz]: | 33.4 |

The dielectric loss is significantly reduced over the reference mixture. The tuneability τ is slightly improved. In all the material quality η is improved significantly.

Mixture Example M2

The medium M2 consists of 90% of host H1 and 10% of compound of Synthesis Example 2.

The dielectric loss is significantly reduced over the reference mixture. The tuneability τ is slightly improved. In all the material quality η is improved significantly.

Mixture Example M3

The medium M3 consists of 90% of host H2 and 10% of compound of Synthesis Example 4. The addition of the compound results in an increase of the figure of merit η by about 10%.

| Compounds | % | Properties | |
|---|---|---|---|
| Compound Ex. 2, | 10.0 | Clearing point [° C.]: | 147 |
| Base mixture H1 | 90.0 | Δn [589 nm, 20° C.]: | |
| Σ | 100 | Δε [1 kHz, 20° C.]: | |
| | | $\gamma_1$ [mPa s, 20° C.]: | |
| | | $\varepsilon_{r,\parallel}$ [20° C., 19 GHz]: | 3.54 |
| | | tan $\delta\varepsilon_{r,\parallel}$ [20° C., 19 GHz]: | 0.0053 |
| | | $\varepsilon_{r,\perp}$ [20° C., 19 GHz]: | 2.45 |
| | | tan $\delta\varepsilon_{r,\perp}$ [20° C., 19 GHz]: | 0.0095 |
| | | τ [20° C., 19 GHz]: | 0.306 |
| | | η [20° C., 19 GHz]: | 32.4 |

| Compound | % | Properties | |
|---|---|---|---|
| Compound Ex. 4, | 10.0 | Clearing point [° C.]: | 95 |
| Base mixture H2 | 90.0 | $\varepsilon_{r,\parallel}$ [20° C., 19 GHz]: | 2.55 |
| $\Sigma$ | 100 | tan $\delta\varepsilon_{r,\parallel}$ [20° C., 19 GHz]: | 0.0043 |
| | | $\varepsilon_{r,\perp}$ [20° C., 19 GHz]: | 2.29 |
| | | tan $\delta\varepsilon_{r,\perp}$ [20° C., 19 GHz]: | 0.0115 |
| | | $\tau$ [20° C., 19 GHz]: | 0.101 |
| | | $\eta$ [20° C., 19 GHz]: | 8.8 |

The dielectric loss is significantly reduced over the reference mixture. The tuneability $\tau$ is kept almost constant. In all the material quality $\eta$ is improved significantly.

Mixture Example M4

The medium M4 consists of 90% of host H2 and 10% of compound of Synthesis Example 3.

| Compound(s) | | Properties | |
|---|---|---|---|
| Compound Ex. 3, | 10.0 | Clearing point [° C.]: | 81 |
| Base mixture H2 | 90.0 | $\varepsilon_{r,\parallel}$ [20° C., 19 GHz]: | 2.58 |
| $\Sigma$ | 100 | tan $\delta\varepsilon_{r,\parallel}$ [20° C., 19 GHz]: | 0.0054 |
| | | $\varepsilon_{r,\perp}$ [20° C., 19 GHz]: | 2.30 |
| | | tan $\delta\varepsilon_{r,\perp}$ [20° C., 19 GHz]: | 0.0128 |
| | | $\tau$ [20° C., 19 GHz]: | 0.110 |
| | | $\eta$ [20° C., 19 GHz]: | 8.6 |

The dielectric loss is significantly reduced over the reference mixture. The tuneability $\tau$ is slightly improved. In all the material quality $\eta$ is improved significantly.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. From the description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding EP application No. 22192616.5, filed Aug. 29, 2022, are incorporated by reference herein.

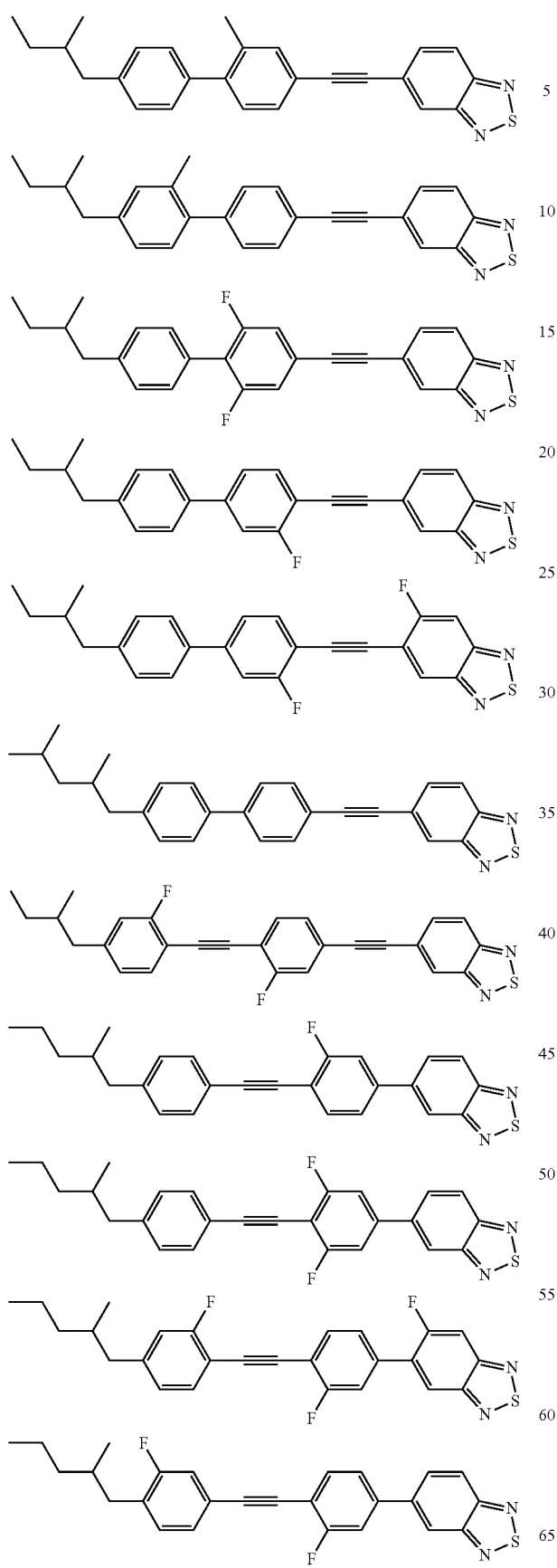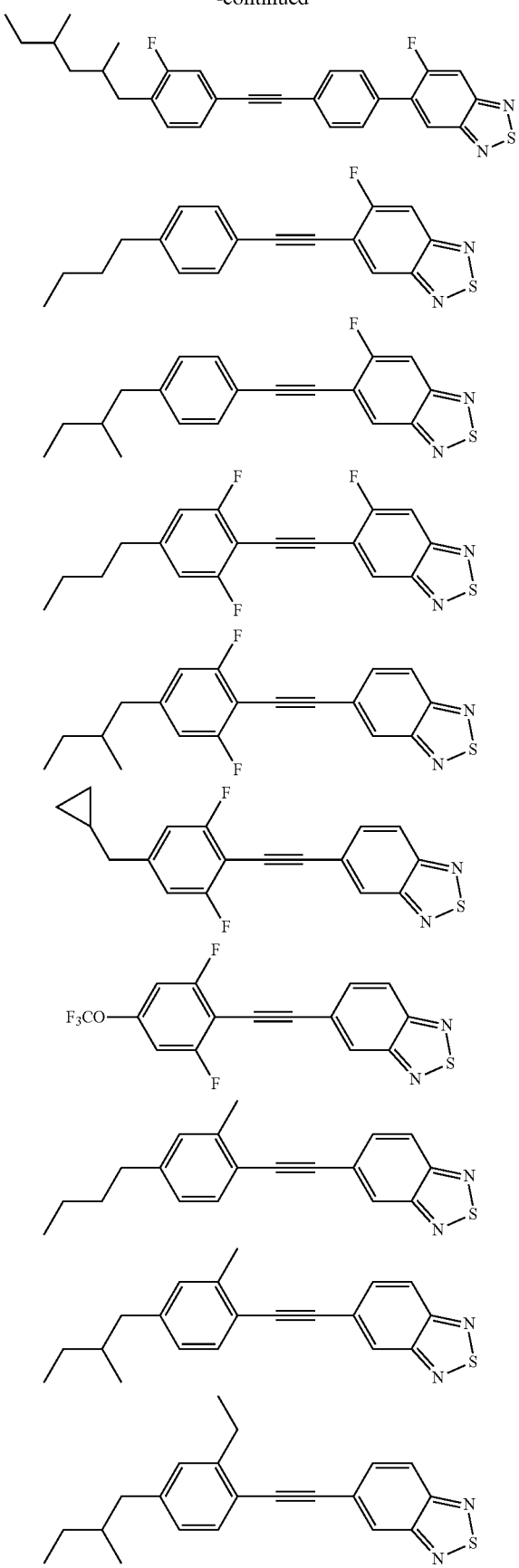

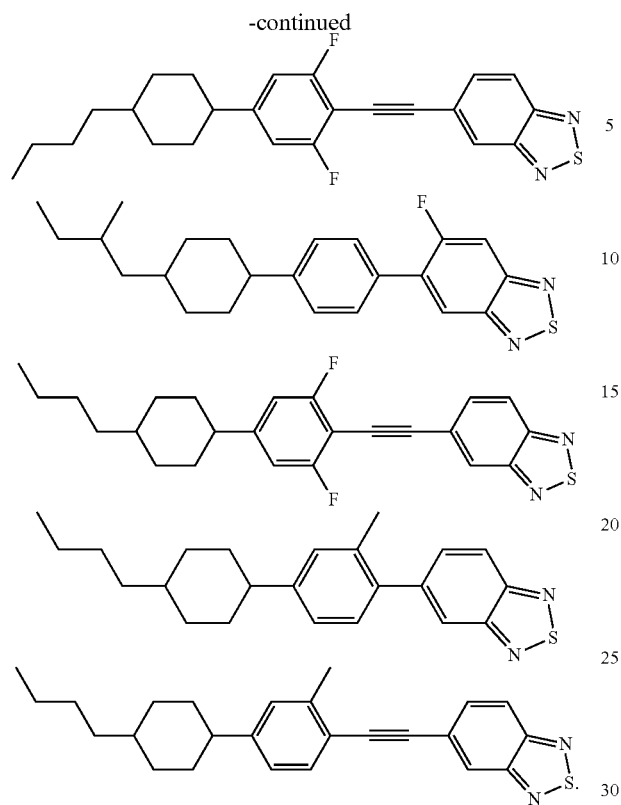

The invention claimed is:

1. A compound of formula I

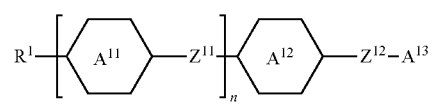

I in which
A¹³ is

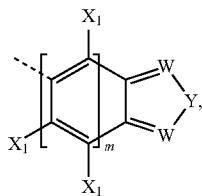

wherein
m is 0 or 1,
W independently on each occurrence is N or CR³,
Y is S or O,
X¹ independently on each occurrence is H, F, —CH₃, C₂H₅ or Cl,
R³ is H, F, Cl, CH₃ or C₂H₅,
R¹ is H, a straight chain alkyl having 1 to 12 C atoms, a branched chain alkyl having 3 to 12 C atoms, a straight chain alkenyl having 2 to 12 C atoms or a branched chain alkenyl having 3 to 12 C atoms, in which one or more CH₂-groups may be replaced by

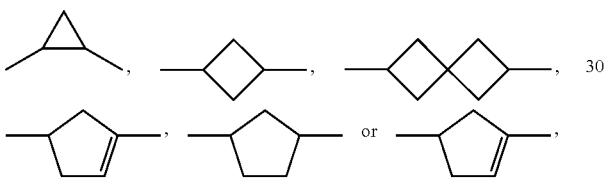

where one or more non adjacent CH₂-groups may be replaced by O and/or S, and where one or more H atoms may be replaced by F,
$Z^{11}$, $Z^{12}$ are, identically or differently and independently on each occurrence, a single bond, —C≡C—, —CH=CH—, —CF=CF—, —CH=CF—, —CF=CH— or —C≡C—C≡C—,

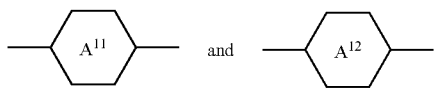

each independently and independently on each occurrence are a radical selected from the following groups:
a) the group consisting of 1,4-phenylene, 1,4-naphthylene, 2,6-naphthylene, tetralin-5,8-diyl, and tetralin-2,6-diyl, in which one or two CH groups may be replaced by N and in which one or more H atoms may be replaced by L,
b) the group consisting of trans-1,4-cyclohexylene, 1,4-cyclohexenylene, bicyclo[1.1.1]pentane-1,3-diyl, 4,4'-bicyclohexylene, bicyclo[2.2.2]octane-1,4-diyl, and spiro [3.3]heptane-2,6-diyl, in which one or more non-adjacent CH₂ groups may be replaced by —O— and/or —S— and in which one or more H atoms may be replaced by F or alkyl having 1 to 6 C atoms,
c) the group consisting of thiophene-2,5-diyl, thieno [3,2-b]thiophene-2,5-diyl, and selenophene-2,5-diyl, each of which may also be mono-or polysubstituted by L, L independently, on each occurrence, is F, Cl, CN, SCN, SF₅ or a straight-chain, in each case optionally fluorinated, alkyl, alkoxy, alkylcarbonyl, alkoxycarbonyl, alkylcarbonyloxy or alkoxycarbonyloxy having 1 to 12 C atoms, or a branched, in each case optionally fluorinated, alkyl, alkoxy, alkylcarbonyl, alkoxycarbonyl, alkylcarbonyloxy or alkoxycarbonyloxy having 3 to 12 C atoms, and
n is 0, 1 or 2.

2. The compound according to claim 1, wherein A¹³ denotes one of the following groups

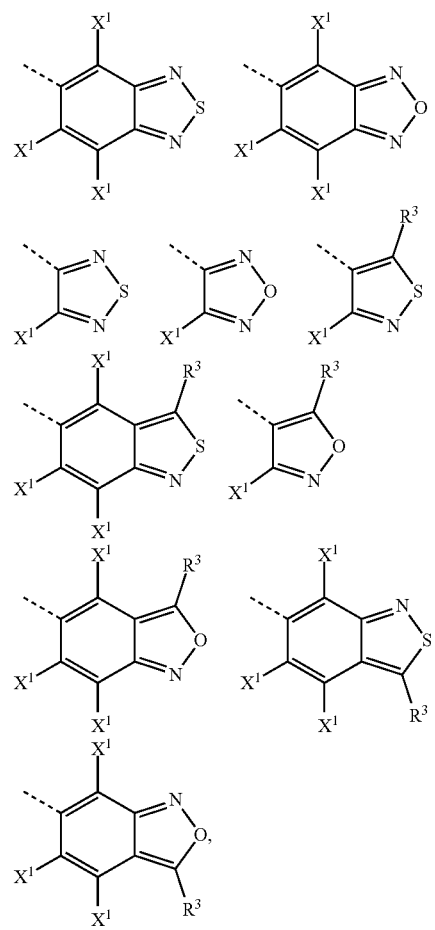

in which X¹ and R³ have the meanings defined as for formula I.

3. The compound according to claim 1, which is of formula Ia or Ib

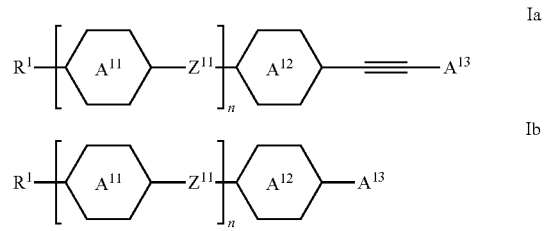

in which R$^1$,

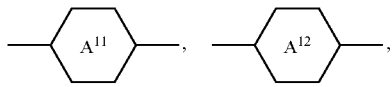

A$^{13}$, n and Z$^{11}$ have the meanings defined as for formula I.

4. The compound according to claim 1, which is of formula Ia-1, Ia-2 or Ia-3

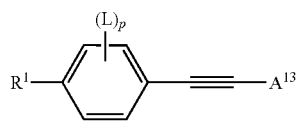  Ia-1

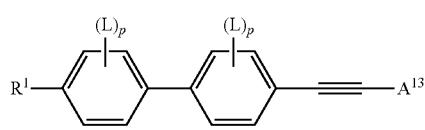  Ia-2

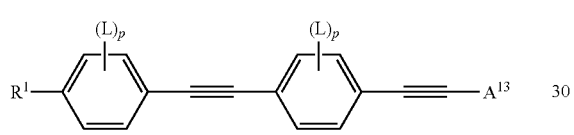  Ia-3 in which R$^1$, A$^{13}$ and L have the meanings defined as for formula I and p is 0, 1, 2, 3 or 4.

5. The compound according to claim 1, which is of formula Ib-1, Ib-2, Ib-3 or Ib-4

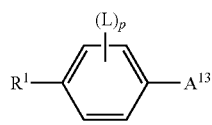  Ib-1

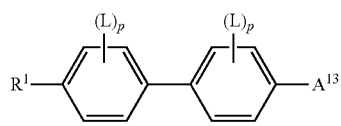  Ib-2

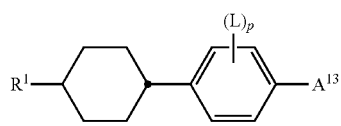  Ib-3

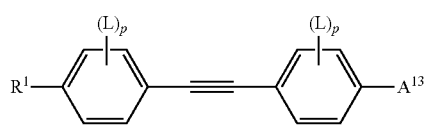  Ib-4 in which R$^1$, A$^{13}$ and L have the meanings defined as for formula I and p is 0, 1, 2,3, or 4.

6. The compound according to claim 1, which is of formula Ic

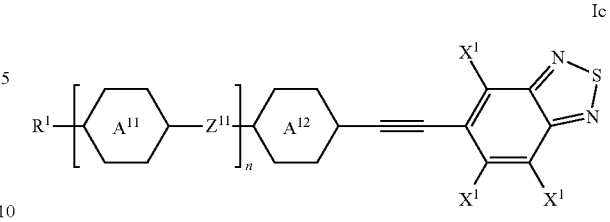  Ic in which
R$^1$,

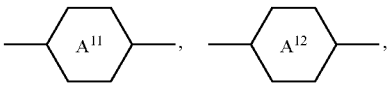

Z$^{11}$, X$^1$ and n have the meanings given as for formula I.

7. The compound according to claim 1, in which

R$^1$ denotes H, non-fluorinated alkyl having 1 to 12 C atoms, or non-fluorinated alkenyl having 2 to 12 C atoms, in which one or more CH$_2$-groups may be replaced by

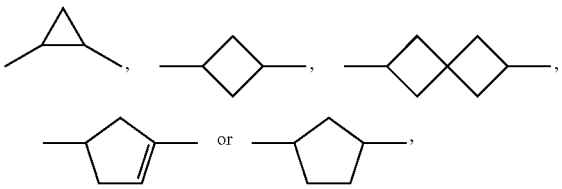

where one or more non-adjacent CH$_2$-groups may be replaced by O,

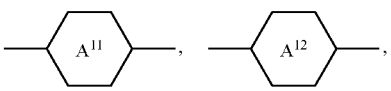

on each occurrence, independently of one another, denote

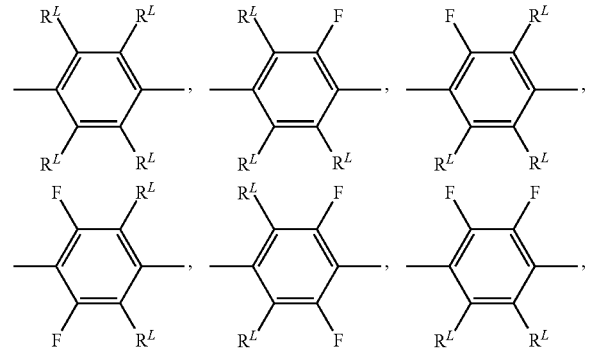

-continued

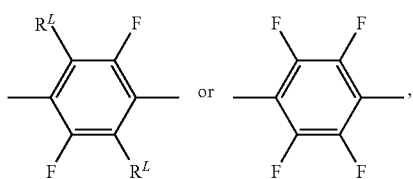

in which $R^L$, on each occurrence, identically or differently, denotes H, Cl or alkyl having 1 to 6 C atoms, or denote

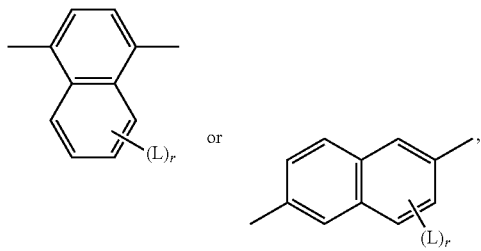

L denotes F or alkyl having 1 to 6 C atoms, and
r is 0, 1, 2, 3, 4, 5 or 6, and wherein

alternatively denotes

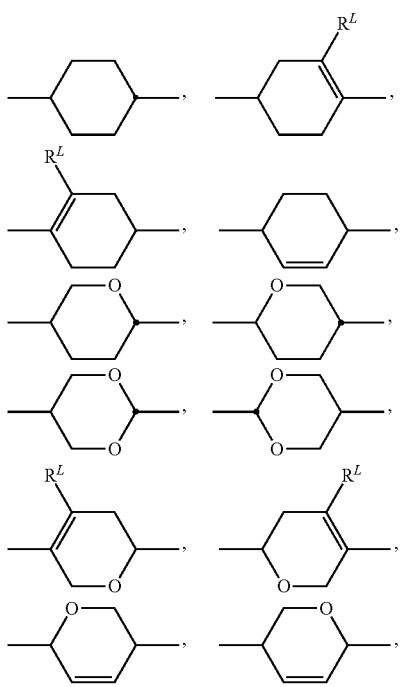

-continued

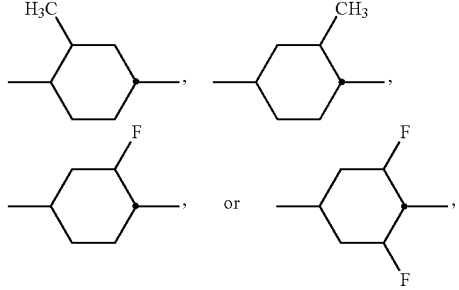

wherein $R^L$ denotes H or methyl.

8. The compound according to claim 1, in which $Z^{11}$ and $Z^{12}$ independently denote —C≡C— or a single bond.

9. A liquid crystal medium comprising one or more compounds according to claim 1.

10. The liquid crystal medium according to claim 9, which further comprises one or more compounds of formula II

II

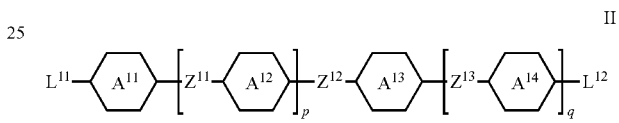

in which $L^{11}$ denotes $R^{11}$ or $X^{11}$, $L^{12}$ denotes $R^{12}$ or $X^{12}$, $R^{11}$ and $R^{12}$ denote, independently of one another, unfluorinated alkyl or unfluorinated alkoxy having 1 to 17 C atoms or unfluorinated alkenyl, unfluorinated alkynyl, unfluorinated alkenyloxy or unfluorinated alkoxyalkyl having 2 to 15 C atoms, $X^{11}$ and $X^{12}$ denote, independently of one another, F, Cl, Br, —CN, —NCS, —SCN, $SF_5$, fluorinated alkyl or fluorinated alkoxy having 1 to 7 C atoms or fluorinated alkenyl, fluorinated alkenyloxy or fluorinated alkoxyalkyl having 2 to 7 C atoms, p and q denote, independently of one another, 0 or 1, $Z^{11}$ to $Z^{13}$ denote, independently of one another, trans-CH═CH—, trans-CF═CF—, —C≡C— or a single bond,

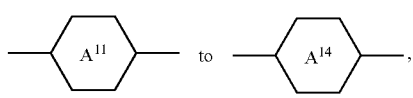

independently of one another, denote

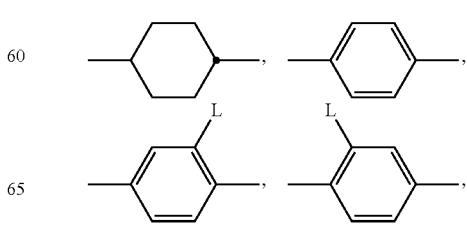

-continued

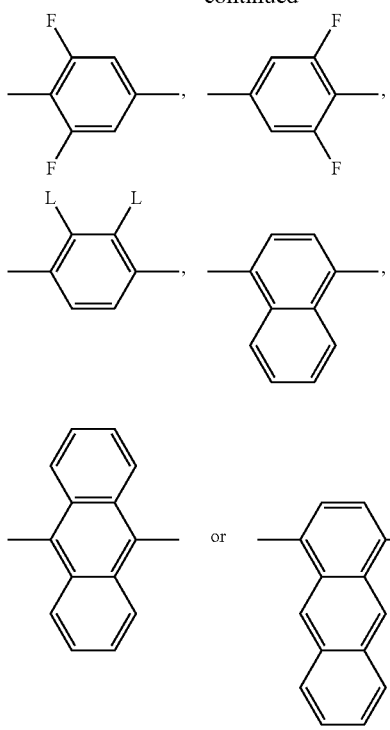

and

L on each occurrence, independently of one another, denotes an unbranched alkyl, having 1 to 12 C atoms, an unbranched alkenyl or alkynyl having 2 to 12 C atoms or a branched alkyl, alkenyl or alkynyl having 3 to 12 C atoms, in which, independently of one another, one or more $CH_2$ groups may be replaced by O, or denotes $C_3$-$C_6$ cycloalkyl, $C_3$-$C_6$ cycloalkenyl, fluorinated alkyl or alkenyl, fluorinated alkoxy or alkenyloxy, F, Cl, Br, CN, NCS, SCN or $SF_5$.

11. A component for high-frequency technology, comprising the liquid crystal medium according to claim 9.

12. The component according to claim 11, which is a liquid-crystal based antenna element, a phase shifter, a tunable filter, a tunable metamaterial structure, a matching network or a varactor.

13. A microwave antenna array, comprising one or more components according to claim 11.

14. The compound according to claim 1, in which $X^1$ independently on each occurrence denotes H, F, —$CH_3$, —$C_2H_5$ or Cl.

15. The compound according to claim 1, which is of formula Ic-1, Ic-2 or Ic-3

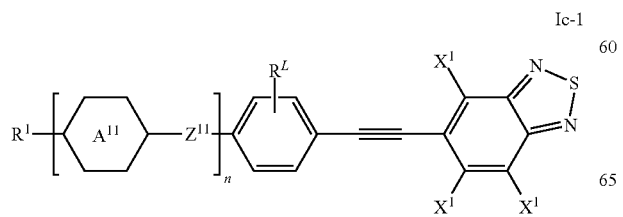

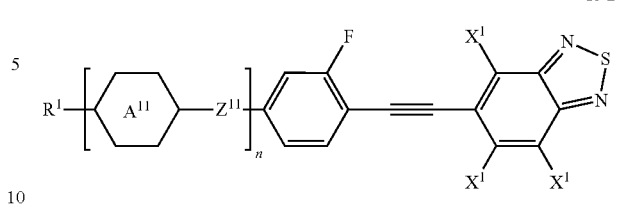

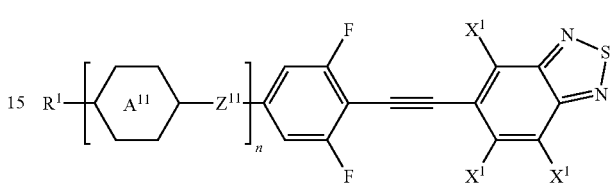

in which $R^1$,

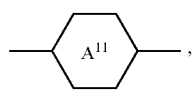

$R^L$, $Z^{11}$, $X^1$ and n have the meanings given as for formula I.

16. The compound according to claim 1, wherein $A^{13}$ denotes one of the following groups

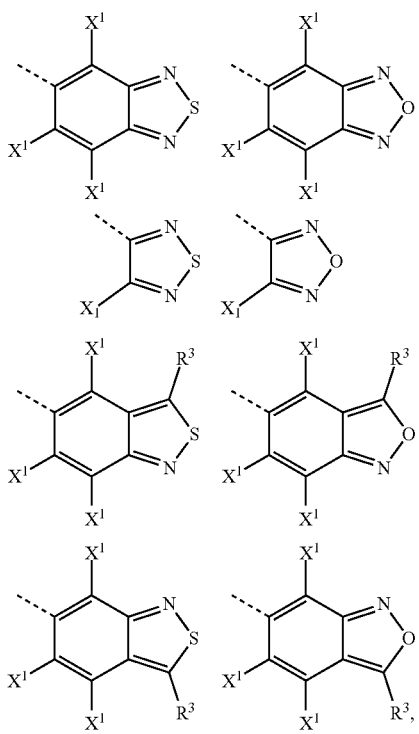

in which $X^1$ and $R^3$ have the meanings defined as for formula I.

17. The compound according to claim 1, which is selected from the following compounds